United States Patent
Aben et al.

(10) Patent No.: US 12,051,192 B2
(45) Date of Patent: Jul. 30, 2024

(54) FLOW ANALYSIS IN 4D MR IMAGE DATA

(71) Applicant: PIE MEDICAL IMAGING BV, Maastricht (NL)

(72) Inventors: Jean-Paul Aben, Limbricht (NL); Leon Ledoux, Landgraaf (NL); Marc Maussen, Beek (NL)

(73) Assignee: Pie Medical Imaging B.V., Maastricht (NL)

( * ) Notice: Subject to any disclaimer, the term of this patent is extended or adjusted under 35 U.S.C. 154(b) by 800 days.

(21) Appl. No.: 16/964,493

(22) PCT Filed: Jan. 24, 2018

(86) PCT No.: PCT/EP2018/051677
§ 371 (c)(1),
(2) Date: Jul. 23, 2020

(87) PCT Pub. No.: WO2019/145027
PCT Pub. Date: Aug. 1, 2019

(65) Prior Publication Data
US 2021/0035290 A1 Feb. 4, 2021

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0263* (2013.01); *A61B 5/0285* (2013.01);
(Continued)

(58) Field of Classification Search
CPC .................... G06T 7/0012; G06T 7/30; G06T 2207/10088; G06T 2207/30104;
(Continued)

(56) References Cited

U.S. PATENT DOCUMENTS

| | | |
|---|---|---|
| 6,252,402 B1 | 6/2001 | Sanfilippo et al. |
| 7,332,912 B2 | 2/2008 | Pittaluga et al. |

(Continued)

FOREIGN PATENT DOCUMENTS

| | | | | |
|---|---|---|---|---|
| CN | 102631196 | 8/2012 | | |
| CN | 106037710 A | * 10/2016 | ............. | A61B 5/026 |

(Continued)

OTHER PUBLICATIONS

Machine translation of CN106037710A1 (Year: 2016).*
(Continued)

*Primary Examiner* — John Villecco
*Assistant Examiner* — Courtney Joan Nelson
(74) *Attorney, Agent, or Firm* — Gordon & Jacobson, P.C.

(57) ABSTRACT

A method for performing flow analysis in a target volume of a moving organ having a long axis, such as the heart, from 4D MR Flow volumetric image data set of such organ, wherein such data set comprises structural information and three-directional velocity information of the target volume over time, the devices, program products and methods comprising, under control of one or more computer systems configured with specific executable instructions: a) deriving from the 4D MR Flow volumetric image data set at least one derived image data set related to the long axis of the moving organ, for example, by using a multi planar reconstruction; b) determining at least one feature of interest in the 4D MR Flow volumetric image data set or in said derived image data set. The feature of interest may be determined, for example, by receiving input from a user or by performing automatic detection steps on the 4D MR Flow volumetric image data set; c) tracking the feature of interest within the 4D MR Flow volumetric image data set or in the derived image data set; d) determining the spatial orientation over time of a (Continued)

plane containing the feature of interest in the 4D MR Flow volumetric image data set; e) performing quantitative flow analysis using velocity information on the plane as determined in step d). A corresponding device and computer program are also disclosed.

39 Claims, 31 Drawing Sheets

(51) Int. Cl.
| | | |
|---|---|---|
| *A61B 5/026* | (2006.01) | |
| *A61B 5/0285* | (2006.01) | |
| *G06N 20/00* | (2019.01) | |
| *G06T 7/33* | (2017.01) | |
| *G06T 7/73* | (2017.01) | |
| *G06T 15/08* | (2011.01) | |
| *G16H 30/40* | (2018.01) | |
| *G16H 50/50* | (2018.01) | |

(52) U.S. Cl.
CPC .......... *A61B 5/7246* (2013.01); *G06N 20/00* (2019.01); *G06T 7/344* (2017.01); *G06T 7/73* (2017.01); *G06T 15/08* (2013.01); *G16H 30/40* (2018.01); *G16H 50/50* (2018.01); *G06T 2207/10096* (2013.01); *G06T 2207/30048* (2013.01); *G06T 2207/30104* (2013.01); *G06T 2210/41* (2013.01)

(58) Field of Classification Search
CPC . G06T 2207/10076; G06T 2207/30048; G06T 7/344; G06T 7/73; G06T 15/08; G06T 2207/10096; G06T 2210/41; A61B 5/026; A61B 5/0044; A61B 2576/023; A61B 5/0013; A61B 5/0285; A61B 5/02028; A61B 5/0205; A61B 5/029; A61B 6/507; A61B 8/0883; A61B 8/5207; A61B 5/0263; A61B 5/7246; G16H 30/40; G16H 50/50; G16H 50/20; G06N 20/00
See application file for complete search history.

(56) References Cited

U.S. PATENT DOCUMENTS

| | | | |
|---|---|---|---|
| 2011/0103665 A1 | 5/2011 | Gulsun et al. | |
| 2011/0142316 A1 | 6/2011 | Wang et al. | |
| 2013/0190592 A1 | 7/2013 | Coppini et al. | |
| 2016/0314581 A1* | 10/2016 | Contini | G06T 7/248 |
| 2017/0084036 A1* | 3/2017 | Pheiffer | G06T 7/35 |
| 2017/0146627 A1* | 5/2017 | Cheng | A61B 5/055 |
| 2017/0178349 A1* | 6/2017 | Ketcha | G06T 7/33 |

FOREIGN PATENT DOCUMENTS

| | | |
|---|---|---|
| CN | 106037710 A | 10/2016 |
| EP | 3086287 A1 | 10/2016 |
| JP | 2002140690 | 5/2002 |
| JP | 2003180654 | 7/2003 |
| JP | 2006314778 | 11/2006 |
| JP | 2012217747 | 11/2012 |
| JP | 2014518139 | 7/2014 |
| JP | 2016-131836 A | 7/2016 |
| WO | 2012153539 | 11/2012 |
| WO | 2014185521 | 11/2014 |

OTHER PUBLICATIONS

Bustamante, Mariana, et al. "Atlas-based analysis of 4D flow CMR: automated vessel segmentation and flow quantification." Journal of Cardiovascular Magnetic Resonance 17.1 (2015): 1-12. (Year: 2015).*

Kayser et al., "MR velocity mapping of tricuspid flow: correction for through-plane motion", J Magn Reson Imaging 1997; 7: 669-673.
Bustamante et al., "Atlas-Based Analysis of 4D Flow CMR: Automated Vessel Segmentation and Flow Quantification", Journal of Cardiovascular Magnetic Resonance, Biomed Central LTD., London, UK, vol. 17, No. 1, Oct. 5, 2015, p. 1-12.
Westenberg et al "Accurate and Reproducible mitral valvular blood flow measurement with three-directional velocity-encoded magnetic resonance imaging", Journal of Cardiovascular Magnetic Resonance 2004;6(4);767-776.
Westenberg et al, "Mitral valve and tricuspid valve blood flow: accurate quantification with 3D velocity-encoded MR imaging with retrospective valve tracking", Radiology 2008; 249:792-800.
Roes et al, "Flow Assessment Through Four Heart Valves Simultaneously Using 3-Dimensional 3-Directional Velocity-Encoded Magnetic Resonance Imaging With Retrospective Valve Tracking in Healthy Volunteers and Patients With Valvular Regurgitation", Invest Radiol. 2009; 44 (10): 669-674.
M. Markl et al, "Time-Resolved Three-Dimensional Phase-Contrast MRI", JMRI 2003 17:499-506.
Uribe et al "New Respiratory Gating Technique for Whole Heart Cine Imaging: Integration of a Navigator Slice in Steady State Free Precession Sequences", Journal of Magnetic Resonance Imaging 34:211-219 (2011).
Markl et al, "4D Flow MRI", J. Magn. Reson. Imaging 36, 1015-1036 (2012).
Lisa M. Sobierajski et al, "Volumetric Ray Tracing", Jan. 1995, p. 11-18.
Michael H. Buonocore, "Visualizing blood flow patterns using streamlines, arrows, and particle paths", Magn Reson Med 1998;40:210-226.
Staring M. et al, DPS, "Pulmonary Vessel Segmentation using Vessel Enhancement Filters", Vessel12 Challenge of ISBI Conference. 2012; p. 1-8.
Metz, C. et al. "Regression-Based Cardiac Motion Prediction From Single-Phase CTA." IEEE Transactions on Medical Imaging 31 (2012): 1311-1325.
Zhuang, "Challenges and methodologies of fully automatic whole heart segmentation: a review", Journal of Healthcare Engineering 2013; 4(3): 371-408.
Crum et al, "Non-rigid image registration: theory and practice", The British Journal of Radiology; 77 (2004), S140-S153.
Zhuang et al, "A Registration-Based Propagation Framework for Automatic Whole Heart Segmentation of Cardiac MRI", IEEE Transaction on Medical Imaging Sep. 2010;29(9):1612-25.
Bakhshinejad et al, "Merging computational fluid dynamics and 4D Flow MRI using proper orthogonal decomposition and ridge regression", Journal of Biomechanics, Jun. 14, 2017;58:162-173.
Rispoli et al, "Computational fluid dynamics simulations of blood flow regularized by 3D phase contrast MRI", Biomedical Engineering 2015;Online;14(1):110, pp. 1-23.
LeCun et al., "Deep learning", Nature 521 (7553) (2015), p. 436-444.
Wolterink et al, "Automatic coronary artery calcium scoring in cardiac ct angiography using paired convolutional neural networks", Medical Image Analysis 2016, p. 123-136.
Maffessanti et al "Three-dimensional dynamic assessment of tricuspid and mitral annuli using cardiovascular magnetic resonance", European Heart Journal—Cardiovascular Imaging (2013) 14, p. 986-995.
Dewan et al, "Deformable motion tracking of cardiac structures (DEMOTRACS) for improved MR imaging", Computer Vision and Pattern Recognition, 2001, p. 1-8.
Bo Li et al, "Automatic tracking of mitral valve motion by non-rigid image registration", Journal of Cardiovascular Magnetic Resonance 2008, vol. 10 supplement 1, pp. 1-3.
B.D. de Vos et al, "ConvNet-Based Localization of Anatomical Structures in 3D Medical Images", IEEE Transactions on Medical Imaging, 2017, vol. PP, pp. 1-1.
Ji et al, "Volume tracking using higher dimensional isosurfacing", IEEE Visualization, 2003. VIS 2003., Seattle, WA, USA, 2003, pp. 209-216.

(56) References Cited

OTHER PUBLICATIONS

Calkoen et al.,"Characterization and Improved Quantification of Left Ventricular Inflow Using Streamline Visualization With 4DFlow MRI in Healthy Controls and Patients After Atrioventricular Septal Defect Correction", Journal of Magnetic Resonance Imaging (2014), pp. 1-8.

Calkoen et al, "Characterization and quantification of dynamic left atrioventricular valve regurgitation after atrioventricular septal defect correction with 4D Flow MRI and retrospective valve tracking", Journal of Cardiovascular Magnetic Resonance 2014;16(Suppl 1): p. 138.

Lee, "A simplified B-spline computation routine", Computing 1982, vol. 29, Issue 4, pp. 365-371.

N. Otsu in "A Threshold Selection Method from Gray-Level Histograms", IEEE Transactions on Systems, Man, and Cybernetics, vol. SMC-9, No. 1, pp. 62-66, 1979.

Bock et al, "In Vivo Noninvasive 4D Pressure Difference Mapping in the Human Aorta: Phantom Comparison and Application in Healthy Volunteers and Patients", Magnetic Resonance in Medicine, vol. 66, pp. 1079-1088, 2011.

Eriksson et al, "Semi-automatic quantification of 4D left ventricular blood flow", Journal of Cardiovascular Magnetic Resonance, Feb. 12, 2010;12:9, pp. 1-10.

Xu et al, J. "Medical Image Segmentation Using Deformable Models", SPIE Press, Chapter 3, 2000, 129-174.

Zijlstra et al., "The ideal coronary vasodilator for investigating coronary flow reserve? A study of timing, magnitude, reproducibility, and safety of the coronary hyperemic response after intracoronary papaverine", Catheterization and Cardiovascular Diagnosis, 1986, 298-303.

International Search Report and Written Opinion for International App. No. PCT/EP2018/051677, dated Aug. 14, 2018, 12 pages.

Chinese Office Action and Search Report dated Nov. 24, 2023 of Application No. 201880091770.8.

"Flow Analysis in Cardiac Chambers Combining Phase Contrast, 3D Tagged and Cine MRI", Radomir Chabiniok et al, Functional Imaging and Modeling of the Heart, Springer Berlin Heidelberg, Berlin, Heidelberg, pp. 360-369, (Jun. 20, 2013), ISBN 978-3-642-38898-9, XP047032695.

"A Collaborative Resource to Build Consensus for Automated Left Ventricle Segmentation of Cardiac MR Images", Suinesiaputra et al, Medical Image Analysis, Jan. 2014, vol. 18, Issue 1, pp. 50-62.

"Automated Detection of Left Ventricle in 4D MR Images: Experience From a Large Study," Lin et al., Medical Image Computing and Computer-Assisted Intervention—MICCAI 2006, vol. 4190 of the series Lecture Notes in Computer Science, Springer, pp. 728-735.

"Layered Spatio-Temporal Forests for Left Ventricle Segmentation from 4D Cardiac MRI Data," Margeta et al, Statistical Atlases and Computational Models of the Heart. Imaging and Modelling Challenges, vol. 7085 of the series Lecture Notes in Computer Science, Springer, pp. 109-119.

"Volumetric Image Registration by Template Matching," Ding et al, Proc. SPIE 3979, Medical Imaging 2000: Image Processing, 1235 (Jun. 6, 2000).

"Whole Left Ventricular Functional Assessment from Two Minutes Free Breathing Multi-Slice CINE Acquisition", Usman et al., Physics in Medicine & Biology, Apr. 2015, 60(7), pp. N93-N107.

* cited by examiner coronal axial sagittal

Tricuspid valve

Mitral valve

Aortic valve

Pulmonary valve

FLOW ANALYSIS IN 4D MR IMAGE DATA

FIELD OF THE INVENTION

The invention relates to the technical field of medical imaging, particularly MR cardio imaging, although it can find application in any field where there is the need to quantify flow in a moving object such as in non-destructive testing applications.

STATE OF THE ART

The accurate study, assessment, and characterization of blood flow patterns and pathophysiology in the cardiac valves and in the main vessels of the human anatomy play a role of primary importance in the diagnosis and treatment of cardiovascular dysfunctions.

Stenosis, inlet and outlet valve regurgitation or congenital defects represent few examples in which the cardiovascular function needs a close imaging follow-up to assess the severity of the symptoms and the consequent optimal timing and type of surgical intervention.

One of the most used techniques to analyze blood flow in clinical setting is flow sensitive Magnetic Resonance (MR) imaging.

The intrinsic sensitivity of MR to flow, allows reliable assessment and quantification of vascular hemodynamics and qualitative delineation of flow patterns, without the restriction to anatomic coverage or flow directions. This is normally performed by the acquisition of a number of two-dimensional (2D) phase-contrast Magnetic Resonance Imaging (MRI) planes, also known as 2D MR Flow.

However, this method requires careful planning of the 2D phase-contrast MR image acquisition planes by an experience MR operator. For example, for each heart valve that is being assessed, the operator needs to carefully position a plane that is used during the acquisition. The planning of this plane is of great importance because this plane is static and needs to be placed perpendicular to the blood flow. The fact that the acquisition plane is static means the plane does not move during the entire acquisition of the data. Even if the MR operator manages to place the plane optimally within the patient's anatomy, certain problems still arise. For instance, out of plane motion will occur. This out of plane motion (through plane motion i.e., motion in the longitudinal direction through the acquisition plane positioned at the heart valve of interest, or with other words motion perpendicular to the imaging plane) is a result of movement of the heart during the cardiac cycle. Due to the fact that phase-contrast MR is sensitive to flow, the flow resulting from this through plane motion is encoded in the 2D MR Flow image data. This is a major obstacle for accurate flow estimations, especially in transvalvular regions as reported by previous studies such as Kayser et al "*MR velocity mapping of tricuspid flow: correction for through-plane motion*", J Magn Reson Imaging 1997; 7: 669-673. This through plane motion results in unusable data, hence data is acquired in the static plane but this plane does not contain the correct features (i.e. the valve) anymore. Therefore, this also results in the inability to make a diagnosis based on this data.

Furthermore, due to this high operator dependency, incorrect planning occurs regularly—even in high patient volume centers—, making clinical assessment difficult, and potentially hampering a correct diagnosis.

Furthermore, the operator needs previous knowledge of the flow-encoding direction in order to position the acquisition plane perpendicular to the blood flow. All these aspects result in a time-consuming and error prone process.

An attempt to improve 2D MR Flow was performed in the work of Dewan et al, "*Deformable Motion Tracking of Cardiac Structures (DEMOTRACS) for Improved MR Imaging*", IEEE Conference on Computer Vision and Pattern Recognition, 2007. Dewan et al., estimated the cardiac motion by utilizing valve tracking within 2D long-axis cine MR images which are acquired during an initial scan (Long Axis views), and used the estimated cardiac motion to adaptively re-position the 2D acquisition plane during the 2D MR Flow acquisition. With tracking of the valve is meant following the motion of the valve through different phases of one or multiple heart cycle(s).

The tracking method is based on a predefined database of manual identified anatomical landmarks. This method requires a database with identified anatomical landmarks for specific scan orientations. This results that the database must obtain information for each long axis view used during the tracking). This makes the method heavily dependent on the content of the predefined database, acquisition method and long axis plane orientation.

Further, this work focuses on valve tracking for dynamic acquisition plane positioning for 2D MR Flow acquisitions only. Because this method is applied during a cardiac MR flow acquisition, with the patient inside the scanner, errors in the valve tracking will result in incorrect flow acquisitions and no diagnosis will be possible afterwards.

Time resolved three-dimensional phase contrast MRI (4D MR flow) is an evolving imaging technique used for evaluation of multidirectional flow velocity data. In 4D MR flow, anatomical and three-directional velocity information are acquired for each voxel within a three-dimensional (3D) isotropic volume over time.

This type of data allows the analysis of blood flow from any spatial oriented plane. Therefore, the aforementioned problems of a static analysis plane do not hold anymore, since the plane can be repositioned at each acquired time point (i.e. at each acquired phase during the cardiac cycle) to tightly follow the patient's heart valve with respect to the patient's cardiac and respiratory movements. Due to the cardiac and respiratory movement compensation, and by centering the analysis plane for the object of interest, through plane motion will therefore not occur anymore as taught by Westenberg et al "*Accurate and Reproducible mitral valvular blood flow measurement with three-directional velocity-encoded magnetic resonance imaging*", Journal of Cardiovascular Magnetic Resonance 2004; 6:767-776.

Repositioning of the analysis plane during the cardiac cycle requires tracking of anatomical landmarks. During the introduction of 4D MR Flow imaging technique, 4D MR Flow suffered from limited signal to noise ratio of the anatomical data and resulted in poor detailed outlining of anatomical structures. Therefore, a different strategy had to be adopted to efficiently track anatomical structures movements.

Several authors addressed the problem by manually identifying the valve position on each time frame on two additional MR sequences, for instance Westenberg et al, "*Mitral valve and tricuspid valve blood flow: accurate quantification with 3D velocity-encoded MR imaging with retrospective valve tracking*", Radiology 2008; 249:792-800 and Roes et al, "*Flow assessment through four heart valves simultaneously using 3-dimensional 3-directional velocity-encoded magnetic resonance imaging with retrospective valve tracking in healthy volunteers and patients with val-*

*vular regurgitation*", Invest Radiol 2009; 44: 669-674. Their method requires two additional long axis cine MR acquisitions acquired orthogonal to each other and intersecting with the heart valve of interest, e.g. for the mitral valve a left ventricular two-chamber and four-chamber cine MRI acquisition are required which is standard practice and part of a clinical cardiac MR examination. That is for each valve, two long axis cine datasets have to be acquired. Accurate planning of these long axis cine images is needed to avoid out of plane motion of the valve of interest.

Furthermore, Westenberg et al. and Roes et al. deployed manual annotation of the valve location during the cardiac cycle within the long axis cine MR acquisitions. This approach of manual annotation of valve locations during the cardiac cycle has two important limitations. First, manual annotation makes the tracking results user dependent and scarcely reproducible, and also results in large intra- and inter observer variations. The second limitation of manual annotation of valve location is the long process time required for each case. Considering these limitations, manual valve tracking is impracticable for clinical routine.

An approach to resolve above limitations is introduced in US 20160314581. In that work, a method is disclosed which uses only one additional MR acquisition besides the 4D MR Flow dataset. Instead of using multiple 2D cine MRI, the method requires only one 3D axial cine MRI. Within this 3D axial cine MRI, tracking of the heart valves was deployed in order to obtain the correct valve planes and allowing accurate valvular assessment within the 4D MR Flow image dataset. Although, the method as disclosed in US 20160314581 resolved above mentioned limitation, it still doesn't fit perfectly in the clinical workflow. First, the needed 3D axial cine MRI dataset requires additional MR scanning time. Second, 3D axial cine MRI has limited use in the clinic. Third, the method requires good alignment (registration) of the 4D MR Flow dataset with the 3D axial cine MRI dataset.

There is thus the need for a more efficient approach to perform flow analysis in 4D MR Flow data that allows to resolve, at least partially, the mentioned limitations.

SUMMARY OF THE INVENTION

It is thus an object of embodiments herein to provide improved methods and devices for accurate study and characterization of blood flow patterns in cardiac valves with minimal operator interaction.

In accordance with embodiments herein, devices, computer program products and computer implemented methods are provided for performing flow analysis in a target volume of a moving organ having a long axis, such as the heart, from 4D MR Flow volumetric image data set of such organ, wherein such data set comprises structural information and three-directional velocity information of the target volume over time, the devices, program products and methods comprising, under control of one or more computer systems configured with specific executable instructions:
   a) deriving from the 4D MR Flow volumetric image data set at least one derived image data set related to the long axis of the moving organ, for example, by using a multi planar reconstruction;
   b) determining at least one feature of interest in the 4D MR Flow volumetric image data set or in said derived image data set. The feature of interest may be determined, for example, by receiving input from a user or by performing automatic detection steps on the 4D MR Flow volumetric image data set;
   c) tracking the feature of interest within the 4D MR Flow volumetric image data set or in the derived image data set;
   d) determining the spatial orientation over time of a plane containing the feature of interest in the 4D MR Flow volumetric image data set;
   e) performing quantitative flow analysis using velocity information on the plane as determined in step d).

Embodiments herein also relate to devices, computer program products and computer implemented methods for performing flow analysis in a target volume of a moving organ, such as the heart, from 4D MR Flow volumetric image data set of such organ, wherein such data set comprises structural information and three-directional velocity information of the target volume over time, the devices, program products and methods comprising, under control of one or more computer systems configured with specific executable instructions:
   a) determining at least one feature of interest in the 4D MR Flow volumetric image data set, for example, by performing automatic detection steps (1101) on the 4D MR Flow volumetric image data set.
   b) tracking the feature of interest within the 4D MR Flow volumetric image data set;
   c) determining the spatial orientation over time of a plane containing the feature of interest in the 4D MR Flow volumetric image data set;
   d) performing quantitative flow analysis using velocity information on the plane as determined in step c).

This new approach only uses 4D MR Flow data and does not need any additional datasets to perform the analysis. Furthermore, this new approach does not suffer from any miss-alignment between the 4D MR flow dataset and the dataset used for tracking the valve(s). Moreover, this new approach can also utilize the flow information within the tracking and initiation of the tracking.

Embodiments requiring automatic detection steps are particularly powerful as the interaction with the user is very limited. Such steps may advantageous comprise analysing flow behaviour, flow accelerations and/or flow dynamics using the 4D MR Flow volumetric image data set to determine the location of one or more features of interest.

The flow analysis may be based on quantification techniques selected from a group consisting of: instantaneous streamlines, pathlines, particle tracing, kinetic energy or turbulent kinetic energy or vorticity.

When the organ is the heart, the location of the feature of interest, typically a valve, may be determined by combining information at peak-systole and end-systole.

The automatic detection steps may comprise machine learning to determine the location of one or more features of interest.

The feature of interest may also be determined by receiving user indicated points in the derived image data set and then translated to the derived image data set, eventually adjusted upon user input.

In another embodiment, the derived image data set is obtained by receiving landmark indications either from a user, for example in the form of one or more landmarks the user in a static 3D volume, or by performing automatic generation steps on the 4D MR Flow volumetric image data set.

In a variant, the derived image data set is obtained by generating images parallel to the normal from a plane perpendicular to the flow.

Automatic generation steps may advantageously comprise registering the 4D MR Flow volumetric data set with a generic 3D anatomical surface model with annotated features to use as landmarks.

Tracking of the feature of interest may be advantageously performed on the derived image data set by matching multiple two-dimensional or three-dimensional templates have a variable size depending on image acquisition resolution and/or by means of image registration. Template matching may be performed, for example, by cross correlation.

Optionally, feedback to the user may be provided on the tracking of the feature of interest.

Quantitative flow analysis flow may be based, for example, on flow parameters selected from a group consisting of: mean velocities, forward flow), backward flow, pump blood volume, regurgitation fraction, cardiac output, shunt, streamlines, pathlines, particle tracing, continuous pathlines, vector fields, pressure difference, pressure gradient, wall shear stress, oscillatory shear index, energy loss, kinetic energy, turbulent kinetic energy, vorticity.

Quantitative flow analysis is advantageously performed on one-direction velocity information obtained by reformatting the three-directional velocity information on the tracked plane.

Embodiments also relate to a computer product directly loadable into the memory of a digital computer and comprising software code portions for performing the method according to embodiments herein when the product is run on a computer.

According to an aspect, embodiments relate to a MR apparatus for acquiring 4D MR Flow volumetric image data sets, the apparatus comprising an acquisition module for obtaining Time resolved three-dimensional phase contrast MRI image volumes of the heart of a patient, the apparatus further comprising a processor programmed for performing the method according to embodiments herein to make a quantitative blood flow analysis.

The apparatus is advantageously configured to acquire 4D flow images of a volume containing a heart valve, the processor being programmed to locate such plane in the 4D flow images and make a bi-dimensional flow analysis based on velocity information as projected on such a valve plane.

The orientation of the valve plane may be determined by performing valve tracking after the 4D MR Flow volumetric image data set has been acquired.

In accordance with another embodiment, a system with special focus on the extract feature method as described in step 1102 of FIG. 11 discussed below may also be adapted to blood flow based on a 4D MR flow dataset in other areas of the body, such as, but not limited to coronary arteries, coronary veins, pulmonary arteries, pulmonary veins, aortic artery, vena cava arties.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF A PREFERRED EMBODIMENT

A magnetic resonance imaging apparatus comprises an imaging unit configured to carry out sequential imaging. The apparatus applies a radio-frequency magnetic field onto a subject (i.e. patient) placed in a static magnetic field. A magnetic resonance signal generated from the subject is detected due to the application of the radio-frequency magnetic field. Using the detected signals an image is created.

The magnetic resonance imaging apparatus also includes a gradient coil that adds spatial positional information to a magnetic resonance signal by applying a gradient magnetic field onto the subject.

Using different combinations of radiofrequency pulses and gradients, different MRI sequences can be made. An MRI pulse sequence is a programmed set of changing magnetic gradients. Different pulse sequences allow the radiologist to image the same tissue in various ways, and combinations of sequences reveal important diagnostic information.

Figure 2:
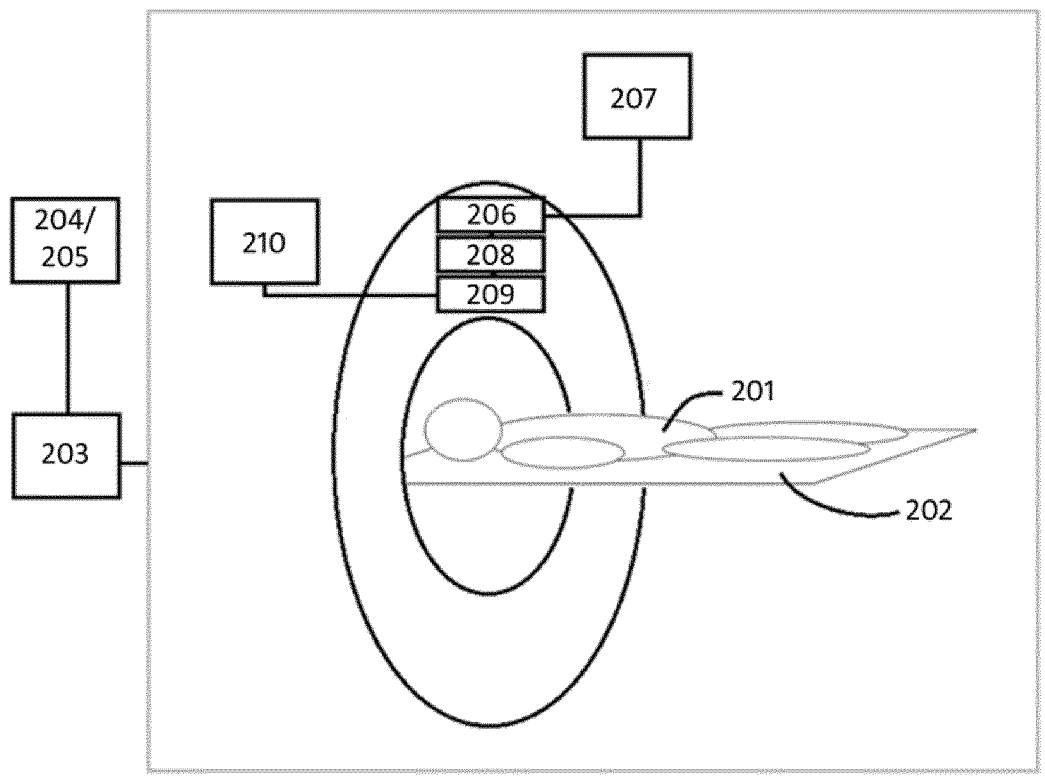
FIG. 2 shows a high-level block-diagram of an MR system.

FIG. 2 illustrates an example of a high-level block diagram of an MRI system.

Portions of the system (as defined by various functional blocks) may be implemented with dedicated hardware, analogue and/or digital circuitry, and/or one or more processors operating program instructions stored in memory.

The MRI system of FIG. 2 includes an adjustable table 202 for a patient 201, a data processing module 203 and a magnet system 206.

The data processing module 203 includes one or more processors and memory that stores program instructions to direct the one or more processors to perform the operations described herein. The data processing module 203 also includes a display to present information to a user, such as the images, indicia, data and other information described herein and illustrated in the figures. The data processing module 203 also includes a user interface to receive inputs from the user in connection with operations herein, such as controlling operation of the imaging apparatus. For instance, scan parameters can be selected or altered, patient images may be displayed and post-processing can be performed, including, for example, region of interest measurements, flow quantification and visual and/or quantitative control selecting projection perspectives to be used when obtaining complementary images and the like. The data processing module 203 may correspond to or include portions of one or more of the systems described within the patents and publications referenced herein and incorporated by reference.

One of the key aspects of an MRI system is the magnet system 206. The magnet system 206 generally comprises a large tube or a cylindrical magnet. The magnet is typically an electromagnet made from coils of superconducting wire typically helium cooled. The flow of electrical current through these coils produces a magnetic field. Permanent magnets can be used as well. The magnetic field has a certain field strength measured in Tesla. An important aspect of the magnet system 206 is the homogeneity of the magnetic field. That is a magnetic field, which changes very little over the specified region or volume.

However, due to manufacturing imperfections or intervention room problems such as nearby steel posts, distortions of the magnetic field may arise. These inhomogeneities are corrected using a shim system 207. The corrections can either be performed manually or automatically. U.S. Pat. Nos. 6,252,402 and 7,332,912 disclose examples of shimming techniques for systems based on permanent magnets.

In clinical MRI hydrogen, atoms of the human body are of importance. The nucleus of each hydrogen atom possesses spin also called nuclear spin angular momentum. That is, the nucleus of the hydrogen atom constantly rotates around an axis at a constant rate. When placed inside a magnetic field the nucleus the rotation axis tilts to align with the magnetic field.

The strong static magnetic field produced by the magnet system 206 aligns the spins of each hydrogen atom of the human body in a certain frequency that is dependent on the strength of the magnetic field.

Next, a radio frequency system 209 emits a radio frequency pulse (RF-pulse) towards the part of the body being examined, tuned to a specific range of frequencies at which hydrogen protons move. This results that some of the hydrogen protons being moved 180 degrees out of alignment with the static magnetic field and being forced into phase with other hydrogen protons.

The radio frequency system 209 generally comprises transmitting coils. The transmitting coil is usually built into the body of the scanner and transmits the RF-signal, generating an effective field perpendicular to the main magnetic field.

The energy, which is absorbed by different hydrogen atoms in the body, is then echoed or reflected back out of the body. The gradient system 208 is switched on and off to measure the echoes reflecting black out of the patient 201 and thus to localize the tissue signals.

Generally, a gradient system 208 consists of one or multiple gradient coils and gradient amplifiers.

Gradient coils are usually loops of wire or thin conductive sheets on a cylindrical shell lying just inside the bore of an MRI scanner. When current is passed through these coils a secondary magnetic field is created. This gradient field slightly distorts the main magnetic field in a predictable pattern, causing the resonance frequency of protons to vary as a function of position.

Typically, three sets of gradients are used: the x-, y- and z-gradients. Each coil set is driven by an independent power amplifier and creates a gradient field whose z-component varies linearly along the x-, y- and z-direction respectively producing the orthogonal field distortion required for imaging.

A data acquisition system 210 then receives the echoes. The data acquisition system 210 is responsible for measuring the signals from the protons and digitizing them for later post-processing. In general, the data acquisition system 210 consists of a coil, a pre-amplifier and a signal processing system.

The coil detects the induced voltage form the protons following an RF-pulse. The coil is tuned to the particular frequency of the returning signal.

The pre-amplifier is a low-noise high gain amplifier located inside the magnet room or the coil itself in order to be able to process the signals produced by the protons.

Furthermore, the signal processing system provides for instance further amplification of the signal, demodulation into kHz signal, low-pass filer, divided into real and imaginary parts then detected by the analogue-to-digital converters (ADC). By applying an Inverse Fourier transformation (IFT) that converts the signal from the protons as mathematical data (k-space) into a picture that can be interpreted by the clinician.

The storage 204 is used to store the patient images that have been acquired immediately after they have been reconstructed. This is typically done in a universal language (vendor independent) such as DICOM. The storage can be a hard disk or a PACS (picture archiving and communications system) server or a VNA (vendor neutral archive) 205.

Velocity encoding gradient echo imaging, also known as phase contrast imaging, is an MRI technique for quantifying blood flow, hereinafter also referenced as MR Flow acquisition. By measuring the phase shift that occurs as protons in the blood move through a magnetic field, the velocity and direction of the blood can be obtained. Details on the time resolved three dimensional phase contrast MRI sequence is published by M. Markl et al, "*Time-Resolved Three-Dimensional Phase-Contrast MRI*", JMRI 2003 17:499-506. Details on the axial cine MR sequence is published by Uribe et al "*New Respiratory Gating Technique for Whole Heart Cine Imaging: Integration of a Navigator Slice in Steady State Free Precession Sequences*", Journal of Magnetic Resonance Imaging 34:211-219 (2011).

Figure 3:
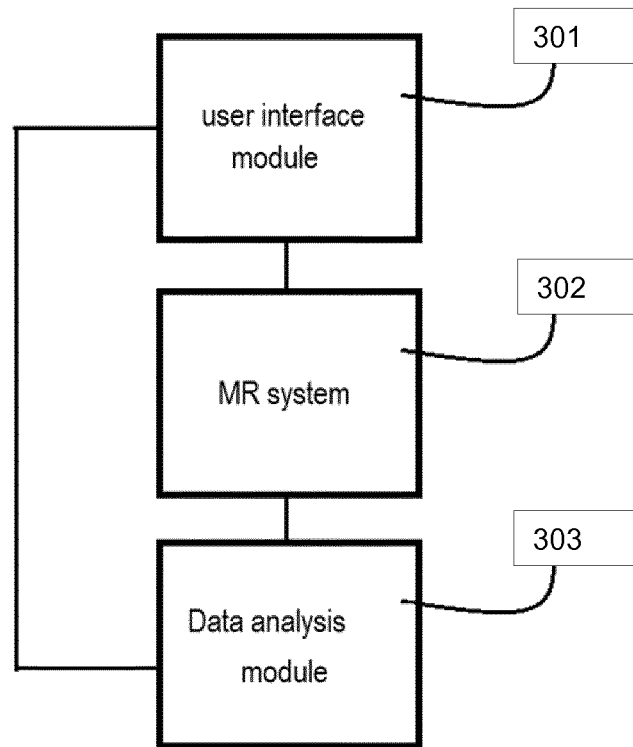
FIG. 3 shows a functional block diagram of an exemplary MRI acquisition of a MR system in accordance with an embodiment herein.

FIG. 3 is a functional block diagram of an exemplary 4D MR Flow acquisition in accordance to an embodiment herein which includes a MR system 302 that operates under commands from the user interface module and provide data to the data analysis module 303.

A clinician or other user acquires an MRI image of a patient 201 and stores this image on a hard disk 204 or a PACS or VNA server 205 in DICOM format.

The MRI system 302 acquires 4D MR Flow data of a volume of interest for instance the heart and the aorta The MR system typically includes a magnet system, a radio frequency system, a gradient system, a data acquisition system and a data storage.

The data analysis module 303 may be realized by a personal computer, workstation, or other computer processing system. The data analysis module 303 processes the acquired 4D MR Flow data of the MRI system 302 to generate, for instance, flow analysis quantification.

The user interface module 301 interacts with the user and communicates with the data analysis module 303. The user interface module 301 can include different kinds of input and output devices, such as a display screen for visual output, a touch screen for touch input, a mouse pointer or other pointing device for input, a microphone for speech input, a speaker for audio output, a keyboard and/or keypad for input, etc.

An embodiment is implemented by the MR system of FIG. 2 as follows. A clinician or other user acquires an MR image of a patient 201 and stores this image on a hard disk 204 or a PACS or VNA server 205 in DICOM format.

The operations, typically performed by the data analysis module 303, can also be carried out by software code that is embodied in a computer product (for example, an optical disc or other form of persistent memory such as a USB drive or a network server).

Figure 1:
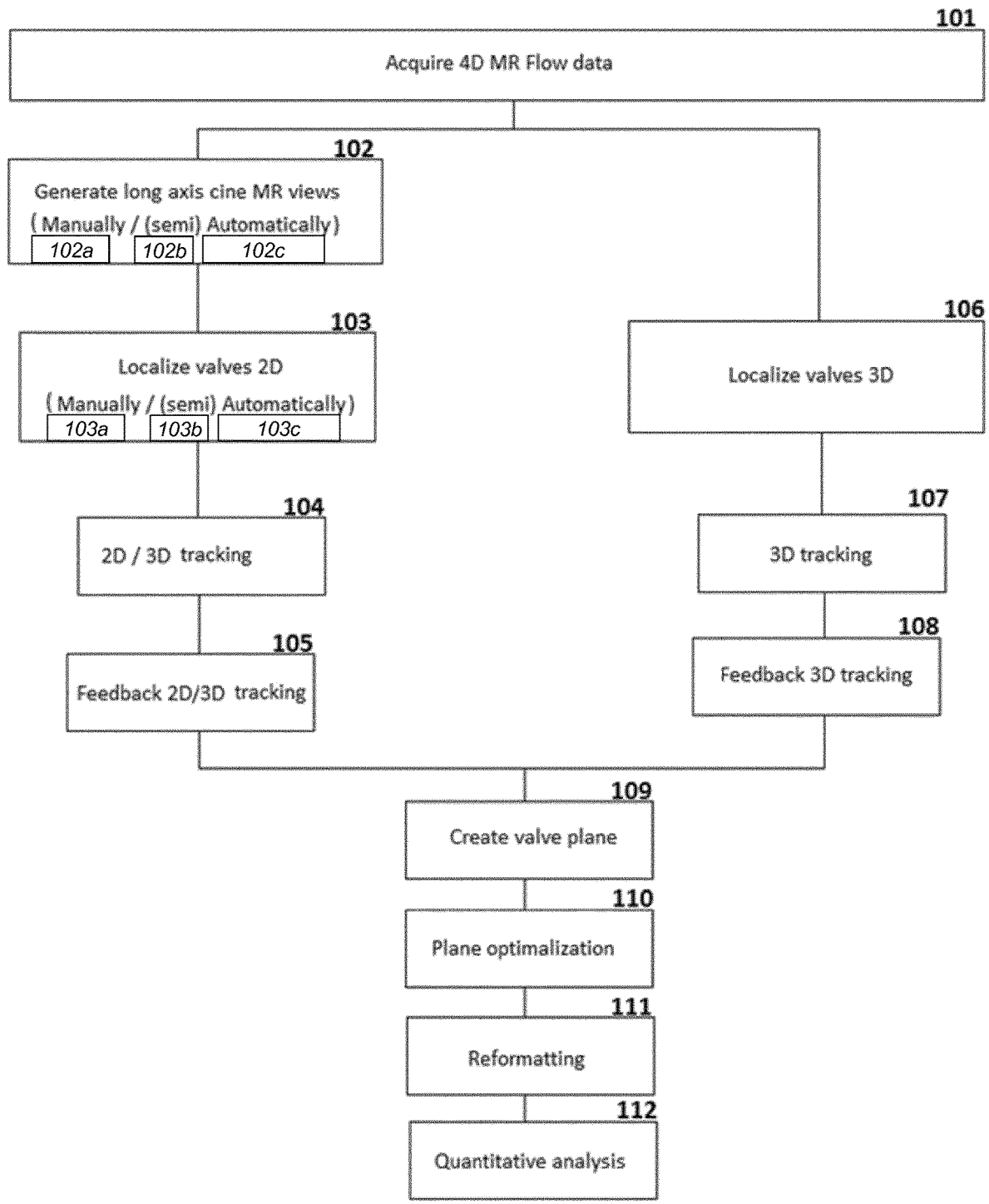
FIG. 1 shows a flowchart of the steps of the invention in a preferred embodiment.

FIG. 1 shows the operations of the method according to an embodiment. These operations can be performed in any logical sequence.

Using 4D MR Flow image dataset as acquired in step 101, one or multiple valves are localized. This can be done in 2D using long axis cine MR views (step 102/103) or directly in 3D (step 106). The defined valve positions are tracked in the 4D MR Flow image dataset (2D: step 104 or 3D: step 104/107). Optionally the user can give feedback regarding the 2D/3D tracking (step 105/108). The spatial orientation and position of the valve plane(s) is then known (step 109). Optionally the valve planes can be optimized to preserve their perpendicularity to the blood flow (step 110). For these (optimized) planes, the velocity data is reformatted (step 111) in order to perform quantitative flow analysis (step 112) and/or to perform 3D visualization of cardiovascular blood flow. In the following section, these steps are explained in more detail.

Step 101: Acquire 4D MR Flow dataset

During a cardiac MR examination, a 4D MR Flow dataset is acquired (step 101 of FIG. 1). The 4D MR Flow dataset refers to phase-contrast MRI acquisition of a 3D volume, with flow-encoding in all three spatial directions that is resolved relative to all three dimensions of space and to the dimension of time along the cardiac cycle (3D+time=4D) (Markl et al, "*4D Flow MRI*", J. Magn. Reson. Imaging 36, 1015-36 (2012)). After the data acquisition is completed, the acquired data yields 3D time resolved magnitude data (3D magnitude data) and three time series representing the three-directional blood flow velocities Vx, Vy, and Vz (3D velocity data). In this type of data, the blood flow through a plane can be studied on any arbitrary positioned plane within the acquired volume as well as the visualization of cardiovascular blood flow.

Before starting the valve tracking process, one or multiple valves of interest need to be determined within the 4D MR Flow dataset. One possible method is by indicating one or multiple valves in 2D long axis cine images which are reconstructed from the 4D MR Flow dataset (step 102/103 of FIG. 1). Another method is done directly in 3D (step 106 of FIG. 1). Examples of these methods are described in detail below.

In current practice, valve assessment (e.g. anatomic, dynamic behavior) is performed in 2D longitudinal cine datasets. Multiple 2D longitudinal cine datasets are separately acquired to allow valve assessment.

Figure 4A:
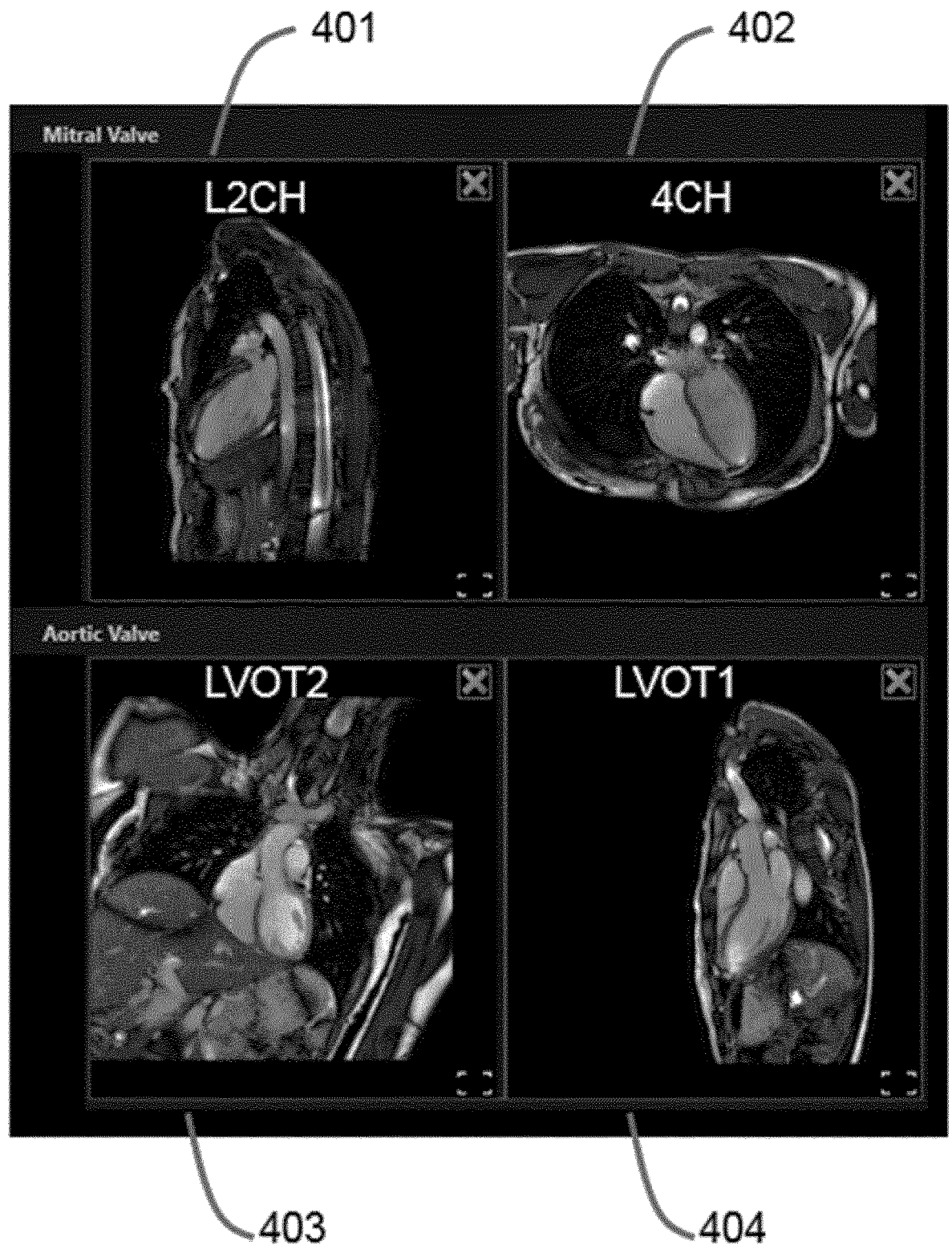
FIGS. 4a and 4b shows the optimal 2D longitudinal cine dataset as needed for valve determination.
Figure 4B:

For each valve of the heart, at least one 2D longitudinal cine dataset is needed that is optimal for valve determination. For instance, for the aortic valve, left ventricle outflow tract sagittal (LVOT1) or coronal (LVOT2) is optimal. For the mitral valve, the four-chamber view (4CH) or the left two chamber view (L2CH) is optimal. For the pulmonary valve, the right ventricle outflow tract sagittal (RVOT1) or coronal view (RVOT2) is optimal. For the tricuspid valve, the right two chamber view (R2CH) or the four-chamber view (4CH) is optimal. As seen in FIGS. 4a and 4b.

In at least one of these optimal views from one or multiple valves, the user indicates the valve position. It is the goal of our invention to provide in a method that only makes use of the 4D MR Flow dataset. Therefore, the required optimal 2D long axis cine images are generated from the 4D MR Flow dataset.

Step 102: Generate 2D Long Axis Cine Images

The generation of the 2D long axis cine images can be done manually, semi-automatically or automatically as shown in step 102 of FIG. 1. For valve tracking, these generated 2D long axis cine images might result in a different orientation as standard acquired within clinical examination to perform valve assessment (2D longitudinal cine datasets). For valve tracking, anatomic features describing the valve motion might not be optimal presented within 2D longitudinal cine datasets, therefore step 102 provides an exemplary method to allow generation of 2D long axis cine images from the 4D MR Flow dataset allowing optimal valve tracking.

Manual Generation of 2D Long Axis Cine Images (102a)

Figure 5:
FIG. 5 shows three orthogonal views (sagittal, coronal and axial) as generated from the 4D MR flow dataset
Figure 5:
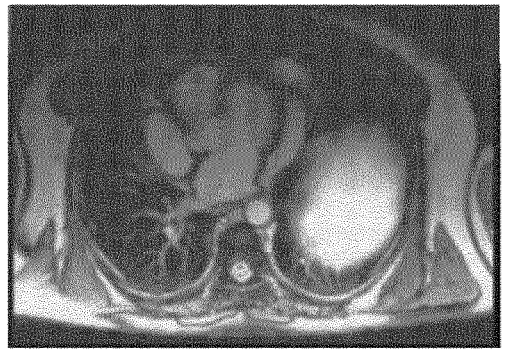
Figure 5:
Figure 5:
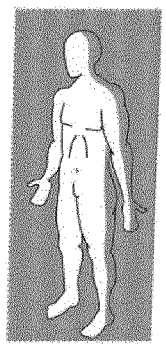
Figure 5:
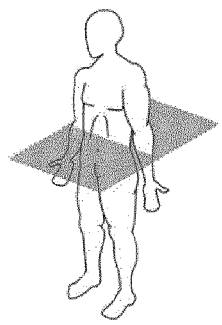
Figure 5:
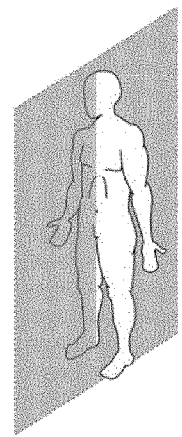
Figure 6:
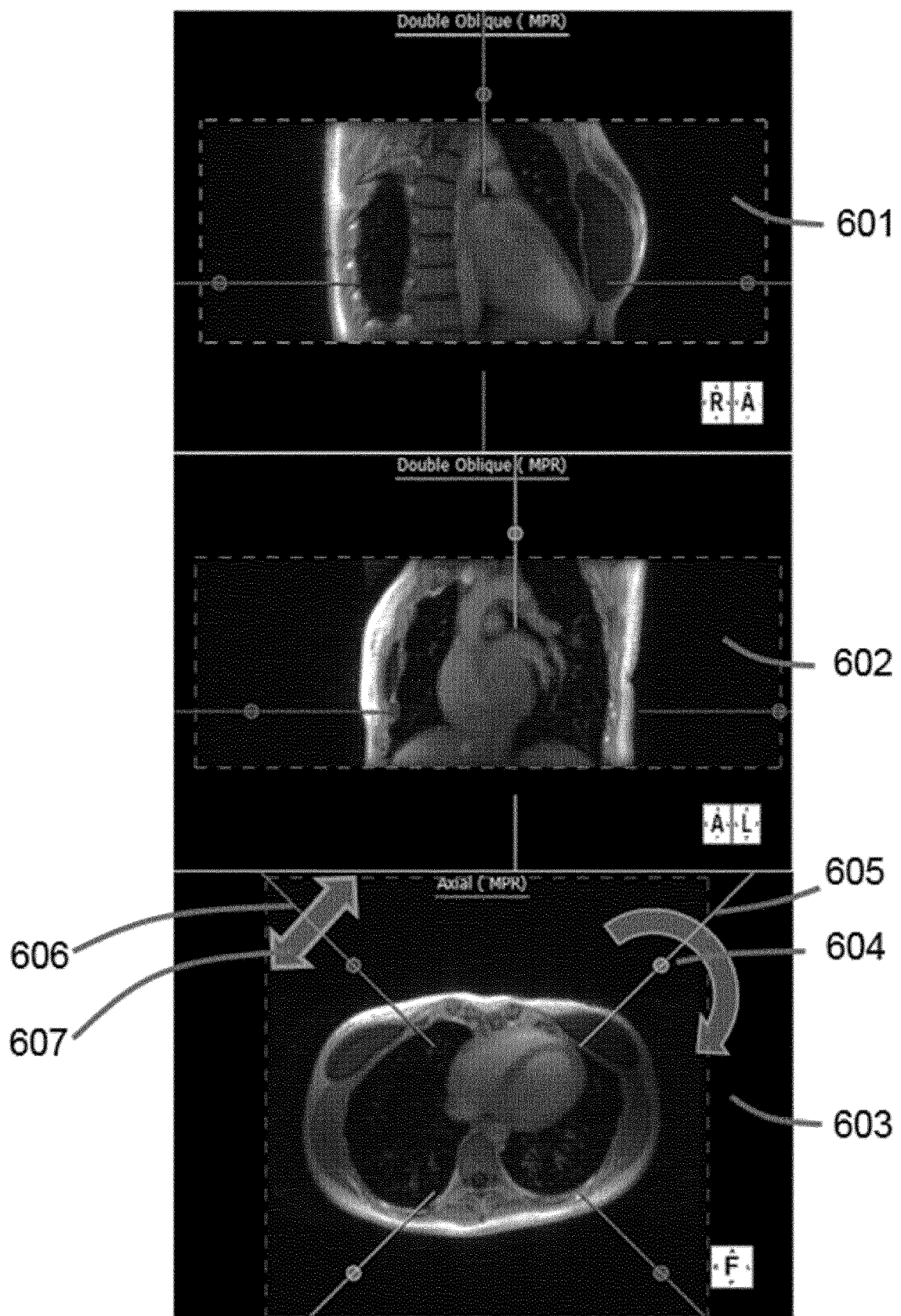
FIG. 6 shows an example of a double oblique multi planar reformatting.
Figure 7:
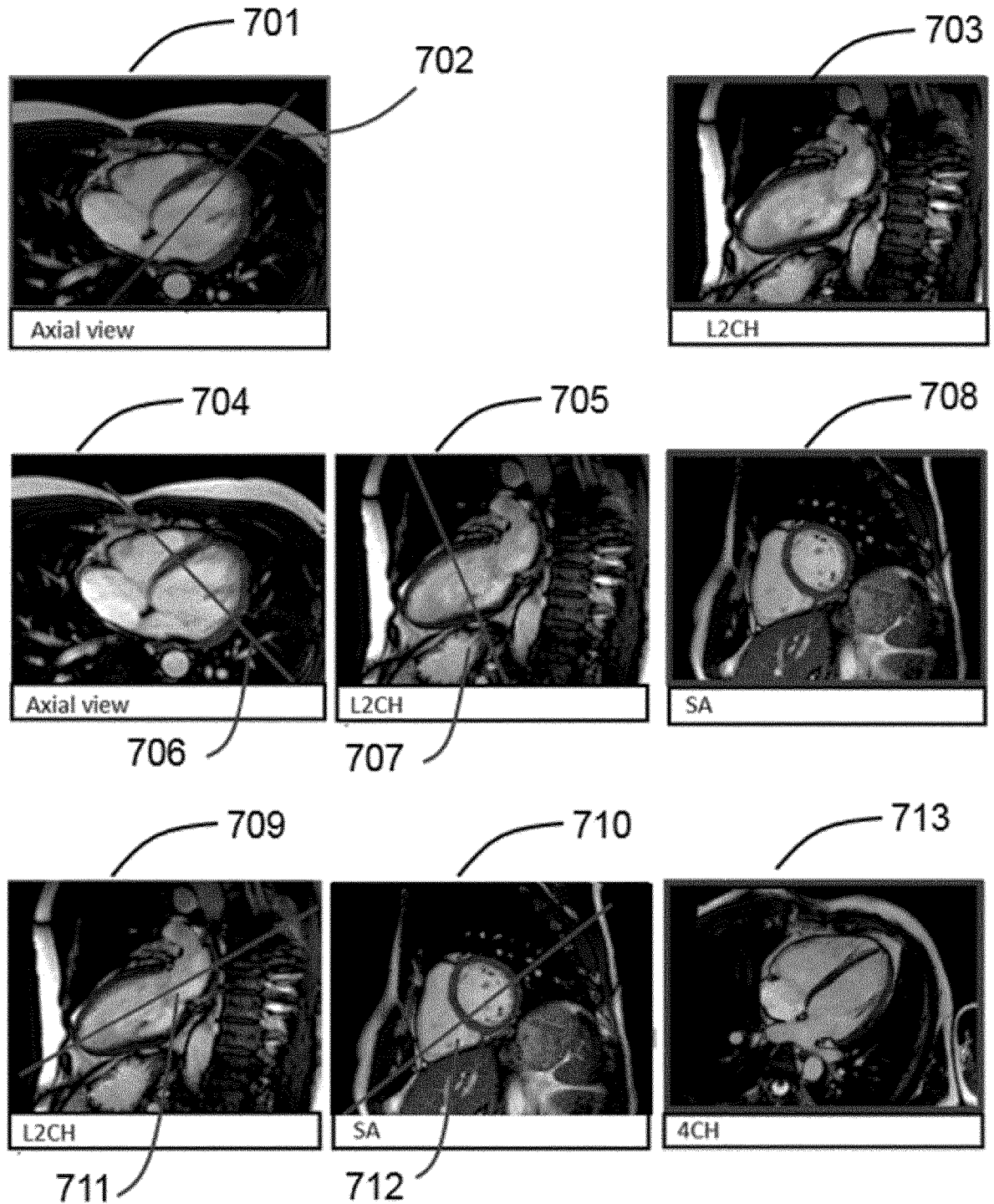
FIG. 7 shows the position of the reference lines as needed for manual generation of 2D long axis cine images optimal for mitral valve and tricuspid valve by means of double oblique multi planar reformatting.
Figure 8:
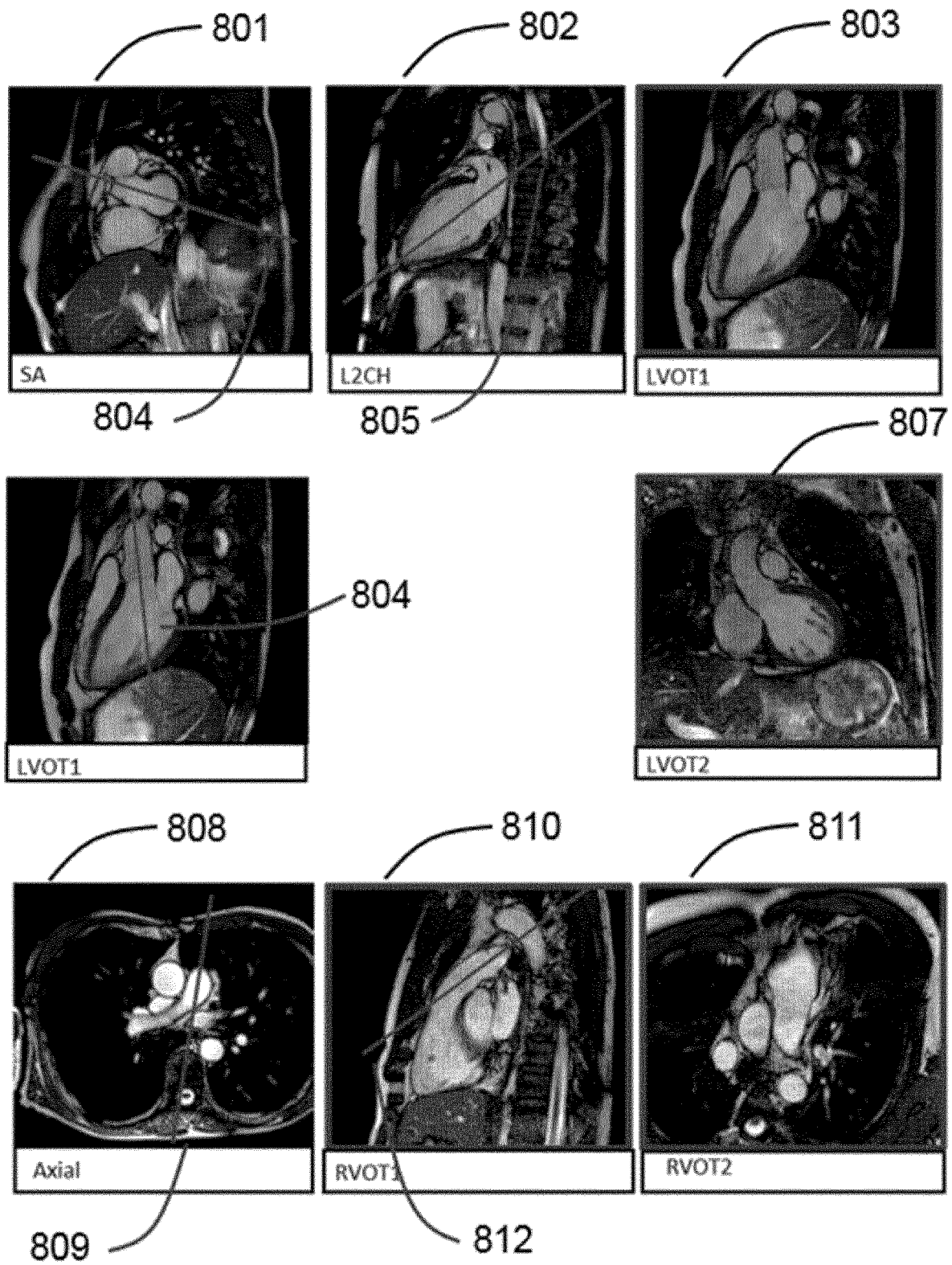
FIG. 8 shows the position of the reference lines as needed for manual generation of 2D long axis cine images optimal for aortic valve and pulmonary valve by means of double oblique multi planar reformatting.

Manual generation of the optimal 2D long axis cines images is done for instance by generating three standard 2D orthogonal views (i.e. sagittal, coronal and axial) using multi planar reconstruction of the 4D MR Flow dataset. Multi planar reconstruction is a post-processing technique to create new 2D images of arbitrary thickness from a stack of images (3D volumetric dataset) in planes other than that of the original stack. FIG. 5 shows an example of generated 2D orthogonal views (i.e. sagittal, coronal and axial) from the 4D MR Flow dataset. In these views, the user is for instance asked to position a line as would be the case during the planning of MR imaging planes in current practice as shown in FIGS. 7 and 8. This line (further referred to as reference line) represents the plane over which the new view will be generated. This is also referred to as double oblique multi planar reconstruction. Double oblique multi planar reconstruction is a type of multi planar reconstruction used in cardiac cross-sectional imaging. It is useful for an accurate assessment of anatomic features, which are not easily visible in the 2D orthogonal views. To form a double oblique plane, the system must be capable of free manipulation of planes. All three standard planes (axial, coronal, and sagittal) should be visible to form the double oblique. The reference lines (or lines) should be fixed at 90 degrees, so being perpendicular to the image view in which the line is drawn. FIG. 6 shows an example of double oblique multi planer reconstruction workflow. In this example, 603 represent the axial view. Since we are using a 3D volumetric dataset, only a slice within this 3D volumetric dataset is shown, the thickness of this slice can be defined and the 2D orthogonal view can be generated by for instance bi-linear interpolation. To allow a different location within this orthogonal view, the user can for instance scroll with the mouse wheel to allow the system to generate a different 2D orthogonal view (at a different depth within the 3D volumetric dataset).

The reference line 605 shows the location in which the image in 601 is generated and reference line 606 shows the location in which the image in 602 is generated. The user can adjust all reference lines. The reference lines can be rotated and/or moved. For instance, the reference line 605 can be rotated around the intersection of reference line 606 and 605, by dragging the point 604. The location of the reference lines can be adjusted for instance by dragging the line 606 and move in perpendicular direction, which can be forced by the system, as indicated by arrow 607. The same will be valid for the reference lines visible in 601 and 602.

By using multi planar reconstruction or double oblique multi planer reconstruction techniques, the 2D long axis cines images can be generated. This is further explained by means of FIG. 7 and FIG. 8. For instance, in the orthogonal axial view, as shown in FIG. 7 (701), the user can scroll through the stack until a view is reached in which the left ventricle (LV) is clearly visible. To obtain the L2CH the user can position a line within the axial view (FIG. 7, 701) parallel to the septum of the heart running through the middle of the LV and through the apex (FIG. 7, 702). Based on the volumetric 4D MR Flow dataset one or more double oblique images views are generated representing the L2CH view within the volumetric 4D MR Flow dataset that runs along the user indicated line (FIG. 7, 703).

Views generated using the user indicated reference line are L2CH views, which can be used to track the mitral valve as shown in FIG. 4*a* (401). The same can be done for the R2CH views using the right ventricle as a landmark, which can be used to track the tricuspid valve as shown in FIG. 4*b* (405).

Then a set of short axis (SA) views (708) can be generated orthogonal to the axial view (704) and L2CH views (705) along reference lines (706 and 707). The 4CH view (713) is generated double oblique to the L2CH view (709) and SA views (710) along the reference line 711 and 712. Reference line 711 is positioned within the L2CH view (709) as a line through the center of the atrium and parallel to the bottom of heart and reference line 712 is position within the SA view (710) as a line through the center of the left ventricle and crossing the right ventricle. In addition, the user can adjust the reference lines as mentioned before. Based on the volumetric 4D MR Flow dataset (101) and the reference lines (711 and 712) one or more double oblique views are generated representing the 4CH views within the volumetric 4D MR Flow dataset. The 4CH view can be used to track the mitral valve as shown in FIG. 4*a* (402) as well as to track the tricuspid valve as shown in FIG. 4*b* (406).

The LVOT1 view (803) can be generated by using the SA view (801) and L2CH view (802) as shown in FIG. 8. The user can for instance scroll through the SA views (801) until the user obtains a view in which the left ventricular outflow track is clearly visible. In this view the user can position a reference line that runs right down the middle of the aorta and divides the left ventricular outflow track in half (804). Within the L2CH view (802) the user can position a reference line that runs through the middle of the LV and through the apex (805). The LVOT1 view is (803) is generated double oblique to the SA view (801) and L2CH views (802) along the reference line 804 and 805. In the LVOT1 view the user can draw a reference line down the middle of the aorta (806) and thus generate the LVOT2 views (807). The LVOT1 and/or LVOT2 view can be used to track the aortic valve as shown in FIG. 4*a* (403, 404).

To generate the RVOT1, in the generated axial images, the user can scroll through the stack until a view is reached in which the main pulmonary artery is clearly visible. To obtain the RVOT1 view (810) the user can position a reference line within the axial view (FIG. 8, 808) through the middle of the pulmonary artery (809). Optionally the user can scroll in the axial view to make sure that the reference line passes through the RVOT. The RVOT2 view (811) is generated double oblique to the axial view (809) and RVOT1 views (810) along the reference line 809 and 812. The RVOT1 and/or RVOT2 view can be used to track the pulmonary valve as shown in FIG. 4*b* (407, 408).

Semi-Automatic Generation of 2D Long Axis Cine Images (102*b*)

Another method for generating optimal 2D long axis cine images is semi-automatically. In this approach, the user indicates a point in the proximity of a feature, for instance the aortic valve. This point can be indicated either in standard 2D orthogonal views, based on multi planar reconstruction and/or based on double oblique reconstruction, or in a 3D volume.

In 2D for instance, three orthogonal views (i.e. sagittal, coronal and axial) are generated using multi-planar-reconstruction or double oblique reconstruction from the 4D MR Flow dataset as described before. The user then indicates the point of interest (e.g. aortic valve or mitral valve) in one of the generated 2D orthogonal slices. The user can identify the slice of interest by scrolling through the generated 2D slices as described by the explanation of FIG. 6. Since the 4D MR Flow datasets consist of a 3D volumetric dataset covering multiple phases of one or more cardiac cycles, all described methods related to multi planar reconstruction and/or double oblique reconstruction allow selection of different phases, even for the generated views from multi planar reconstruction and/or double oblique reconstruction. For instance, the SA view (701) and L2CH view (702) as shown in FIG. 7 can be visualized from different phases within the cardiac cycle. This functionality can be presented to the user for instance by scrolling with the mouse wheel while a specific key is pressed (for instance the 'Alt' key on a Microsoft OS key board).

Figure 9:
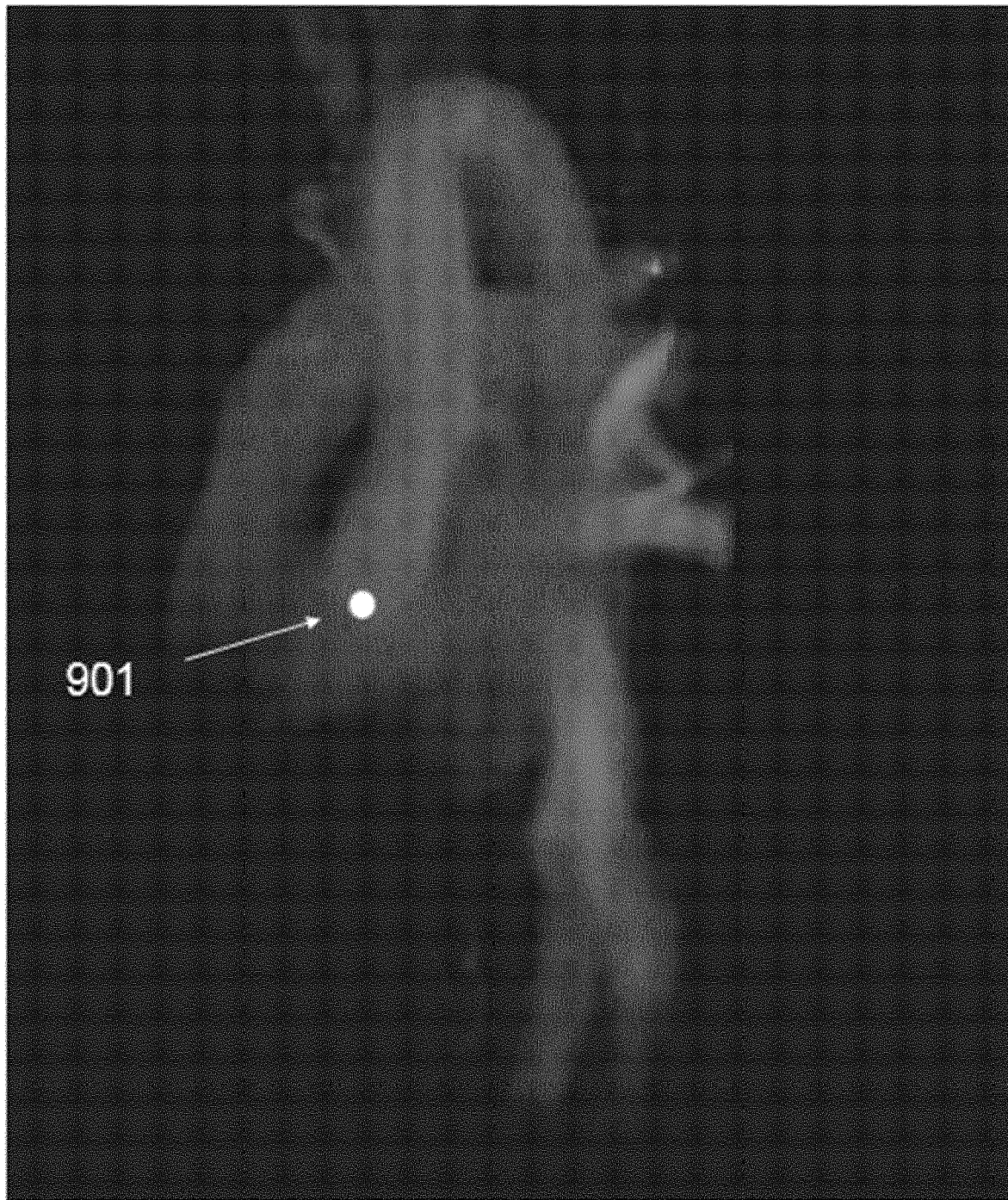
FIG. 9 shows the static volume as created from the 4D MR flow dataset.

For the 3D approach the user for instance indicates a point (901) in a 3D volume rendered image as for instance shown in FIG. 9. The 3D volume can be a static volume. The static volume is generated from the 4D MR Flow dataset and can be for instance a composition of the 3D magnitude data and the 3D velocity data. The magnitude data is used to suppress background velocities. The static volume intensity can for instance be calculated as the time average of the norm velocity weighted by the magnitude. Optionally, the static volume intensities are normalized by dividing the static volume intensities by the maximum static volume intensity that is present. Alternatively, the static volume is calculated within each phase of the cardiac cycle, by weighting the magnitude data with the velocity information within that specific phase, which results in a static volume corresponding to the phase within the cardiac cycle.

The user indicated point can be optimized to best resemble the center point of the valve (feature of interest). This can be done in various ways. One way is to show the user indicated point in the three standard 2D orthogonal views. In these views, the user can then optimize the position of the feature of interest.

Alternatively, the point optimization can be done through ray tracing. In ray-tracing the closest object is found in the viewing direction as described by Lisa M. Sobierajski et al, "*Volumetric Ray Tracing*", January 1995, Proceedings of the 1994 symposium on Volumetric visualization. This can for instance be done using the static volume intensities of the voxels that lie in the viewing direction starting from the user indicated point.

Another method to automatically optimize the user indicated point is described below. This method assumed that the user has indicated a point near the edge of the object of interest. The intensities will have a maximum in the center of the flow area (because the velocities are at their highest value here) and then decrease towards the opposite edge. The voxel that has an intensity equal to full width half maximum (FWHM) in the viewing direction is defined as the opposite edge. Then looking back from the opposite edge point towards the user indicated point the true edge voxel nearest to the user indicated point can be determined again at FWHM. The voxel in the viewing direction that lies in the middle of the two FWHM positions is defined as the center point of the valve. The user indicated point is therefore corrected automatically to this position.

Using this center point (Cp) as established by one of the method described above, a plane can be generated through the user indicated point that is perpendicular to the blood flow by using the velocity information which is available in the 4D MR Flow dataset. From the surrounding voxels of the center point, the average flow direction is determined based on the velocity data within the 4D MR Flow dataset. The average flow direction will correspond to the blood flow direction within the feature of interest and is therefore considered to be the normal vector of the plane (Np).

Figure 10:
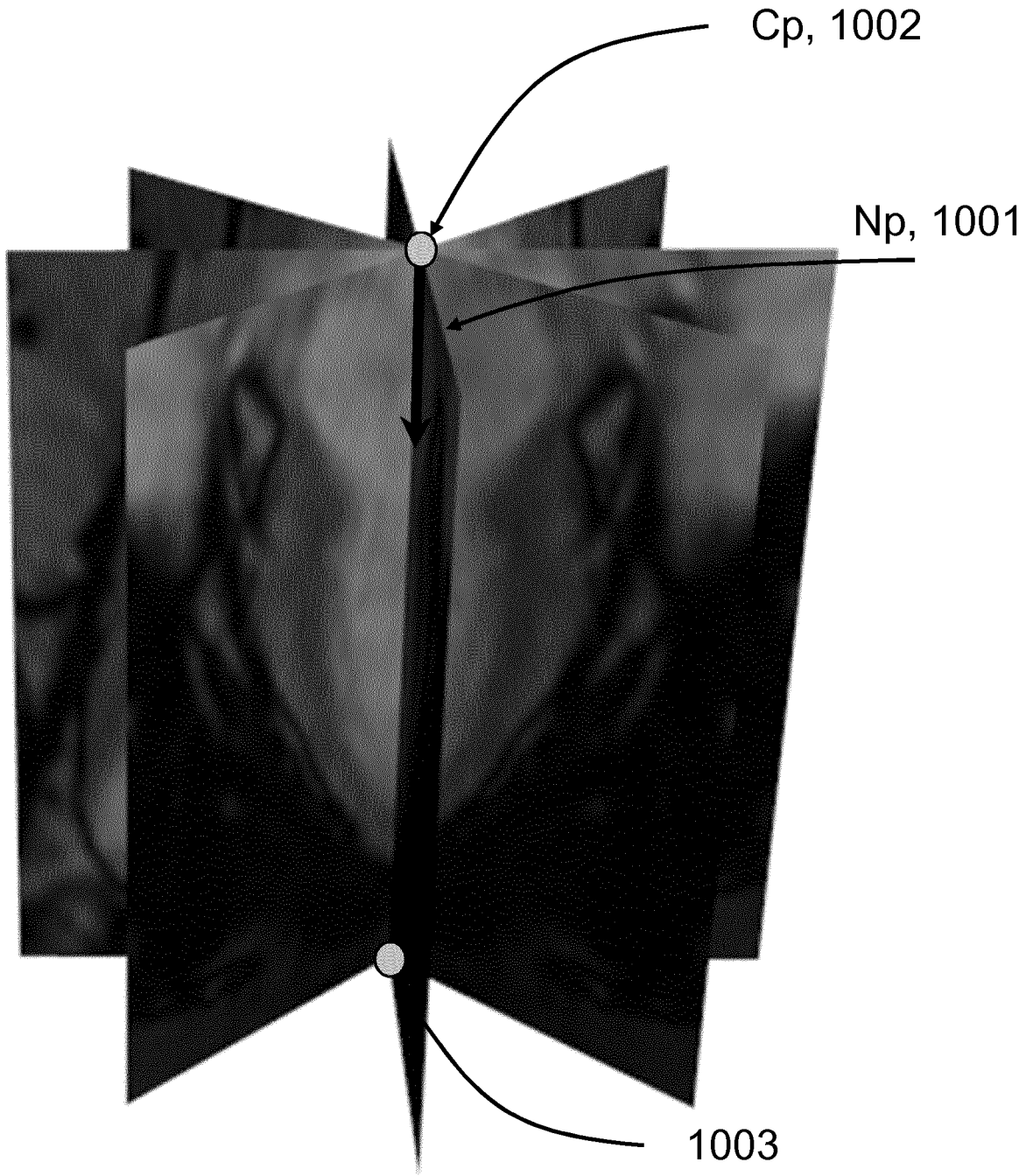
FIG. 10 shows the generated 2D long axis cine images in a 360 degree arc perpendicular to the valve plane.

Perpendicular to this plane, multiple long axis cine images can be generated. These long axis cine images are all parallel to the normal of the plane (Np, 1001) and lie in a 360 degree arc of the center point (Cp, 1002) as can be seen in FIG. 10.

Optionally the user can adjust the normal vector (Np) of the center point by indicating an additional point (1003), for instance at the apex. This ensures that the generated long axis cine images run along the long axis of the heart.

The user can then scroll through the long axis cine images and indicate the valve points in the most optimal long axis cine image. The user can also tilt and translate the planes in order to obtain a more optimal view if necessary.

This approach can be done for one or multiple valves, therefore obtaining optimal 2D long axis cine images for the aortic, mitral, pulmonary and/or tricuspid valve.

Automatic Generation of 2D Long Axis Cine Images (102*c*)

Another method for generating optimal 2D long axis cine images is fully automatically. This approach consists of three steps as presented in flowchart within FIG. 11.

Figure 12A:
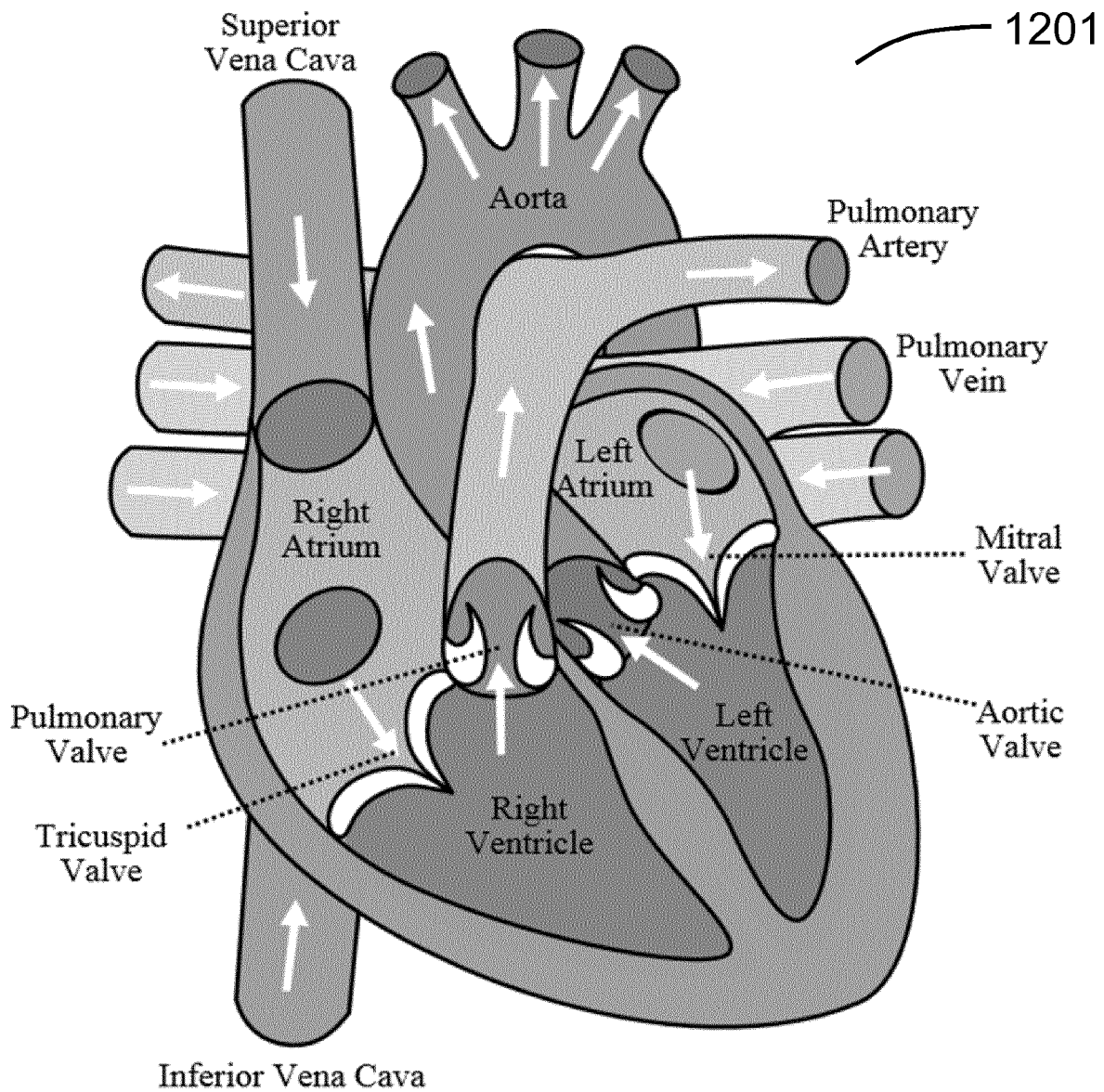
FIG. 12a shows the anatomy of the heart.
Figure 12B:
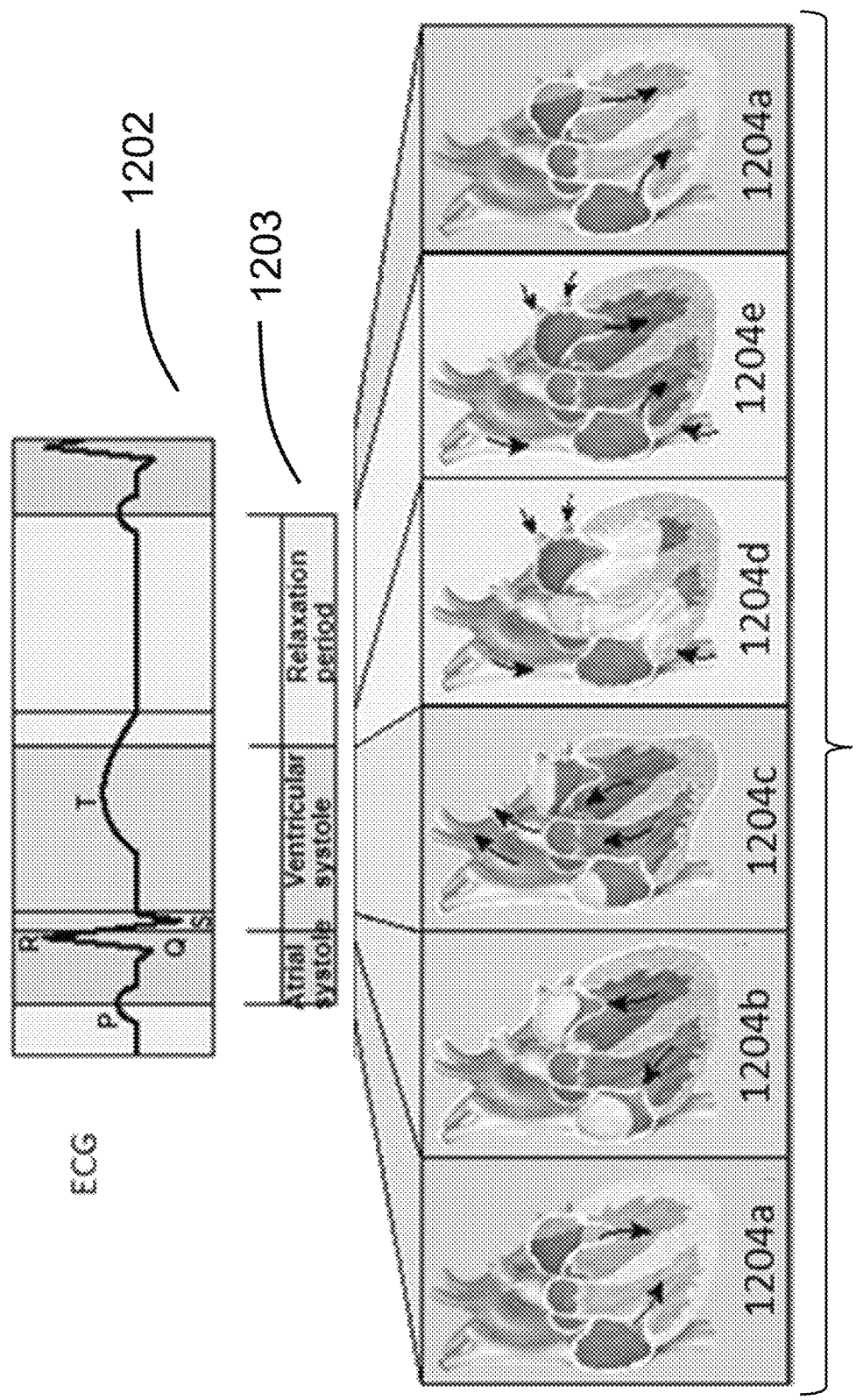
FIG. 12b shows the different phases of the heart chambers during a cardiac cycle.

The first step 1101 localizes one or multiple valves within the 4D MR Flow dataset. This step utilizes the difference in flow behavior, accelerations and flow dynamics within the heart during the cardiac cycle. The heart pumps oxygenated blood to the body and deoxygenated blood to the lungs. There is one atrium and one ventricle for each circulation, and with both a systemic and a pulmonary circulation there are four chambers in total: left atrium, left ventricle, right atrium and right ventricle. The right atrium is the upper chamber of the right side of the heart. The blood that is returned to the right atrium is deoxygenated (poor in oxygen) and passed into the right ventricle to be pumped through the pulmonary artery to the lungs for re-oxygenation and removal of carbon dioxide. The left atrium receives newly oxygenated blood from the lungs as well as the pulmonary vein which is passed into the strong left ventricle to be pumped through the aorta to the different organs of the body, see also FIG. 12*a* (1201). During a cardiac cycle as shown in FIG. 12*b* (1202, 1203), five main states of the heart can be identified (1204), which are: arterial contraction (1204*a*), isovolumetric contraction (1204*b*), ventricular ejection (1204*c*), isovolumetric ventricular relaxation (1204*d*) and ventricular filling (1204*e*). During the arterial contraction state (1204*a*), the atrial valves (mitral, tricuspid) are open and the ventricular valve (aorta, pulmonary) are closed. Blood flows from the atrial chambers in the ventricular chambers. When assuming a heart rate of 75 beat per minute, the arterial contraction state (1204*a*) takes approximately 0.1 seconds. During the isovolumetric contraction state (1204*b*), which is very short and approximately 0.02 seconds, all four valves are closed and the ventricles begin to contract. During the ventricular ejection state (1204*c*), the ventricular valves are open and the atrial valves are closed. Blood is pumped from the ventricular chambers to the lungs (through the pulmonary artery) and to the organs of the body (though the aortic artery) during the ventricular ejection state and this state takes approximately 0.3 seconds. During the isovolumetric ventricular relaxation state (1204*d*), which is very short and approximately 0.02 seconds, all four valves are closed. During the ventricular filling state (1204*e*), the ventricular valves are closed and the atrial valves are open. Blood flows from the major veins (pulmonary veins and vena cava) into the atria's and from there into the ventricles. The ventricular filling state (1204*e*) takes approximately 0.4 seconds. The cardiac cycle is can also be identified as two phases; systole and diastole phase. Systole includes the isovolumetric contraction (1204*b*) and the ventricular ejection phase (1204*c*), as diastole includes the isovolumetric ventricular relaxation (1204*d*) and ventricular filling (1204*e*) and the arterial contraction phase (1204*a*).

Figure 13A:
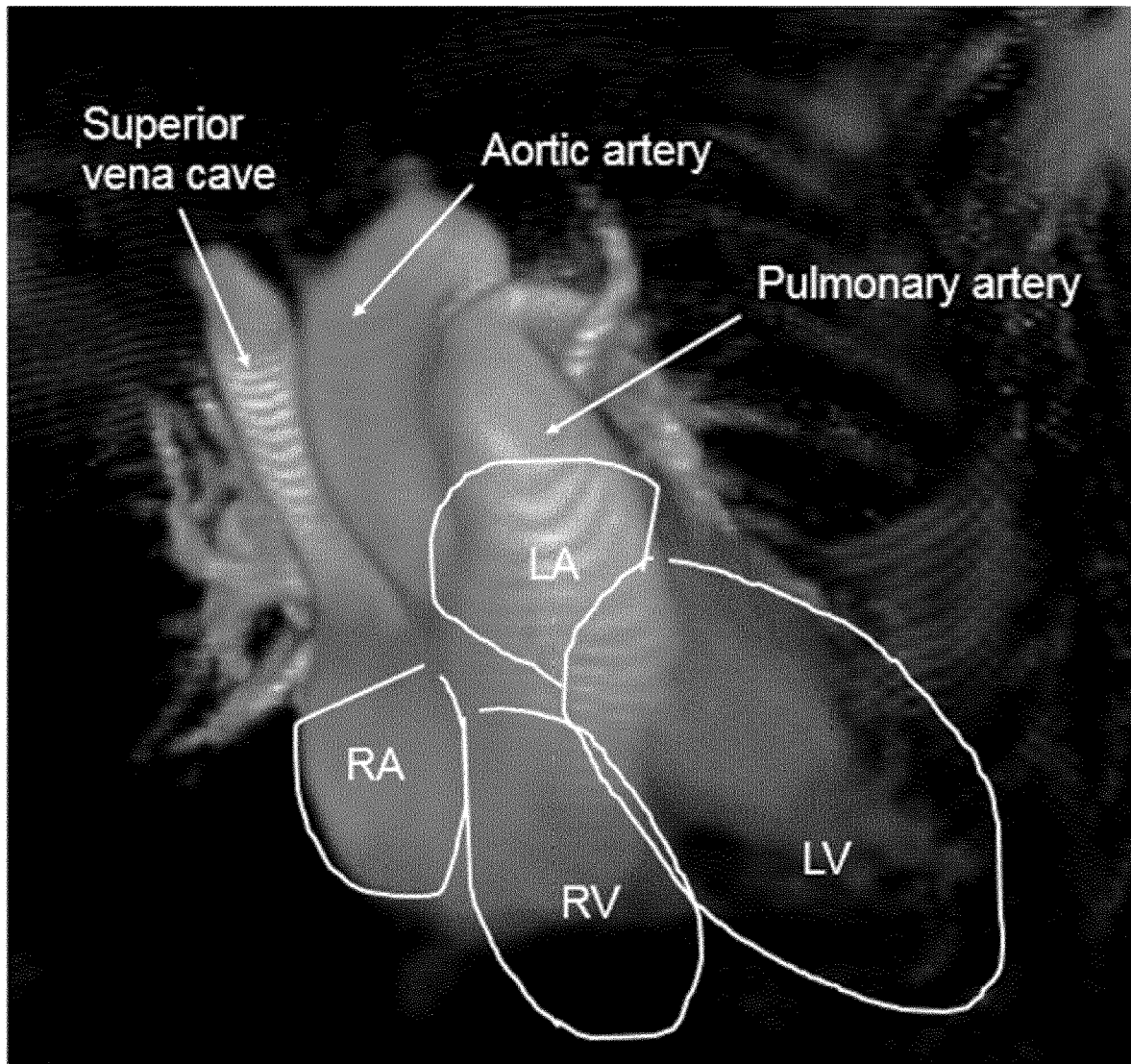
FIG. 13a shows the volume rendered view of the 4D MR Flow dataset covering the heart.
Figure 13B:
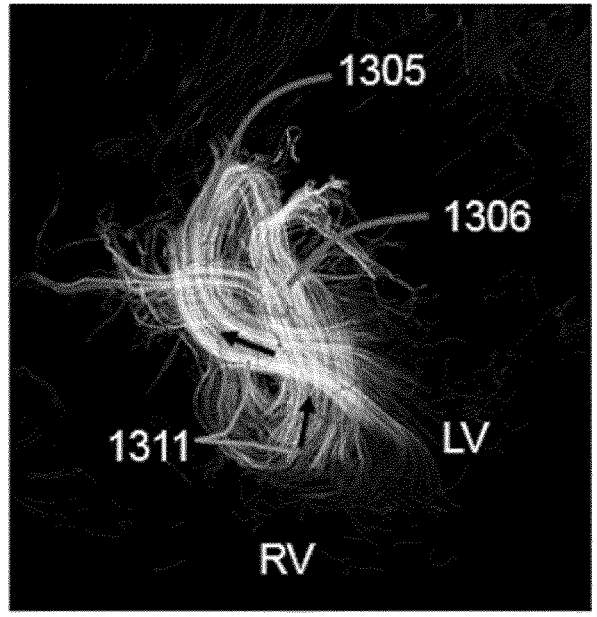
FIG. 13b shows the streamlines within the 3D volume at different phases within the cardiac cycle.
Figure 13B:
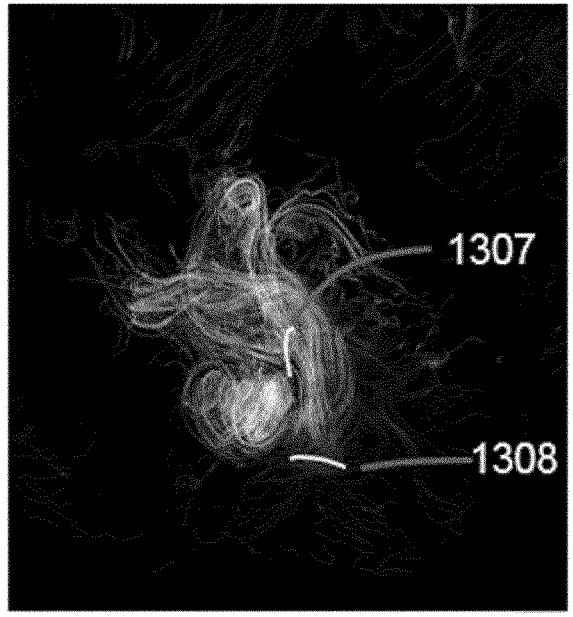
Figure 13B:
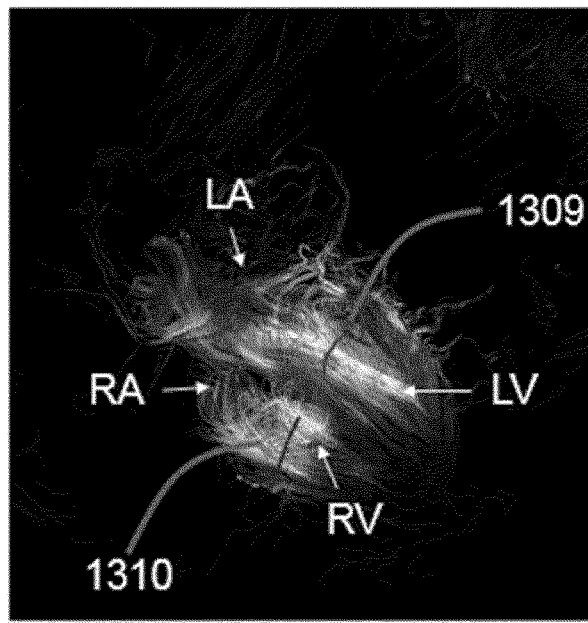
Figure 13B:
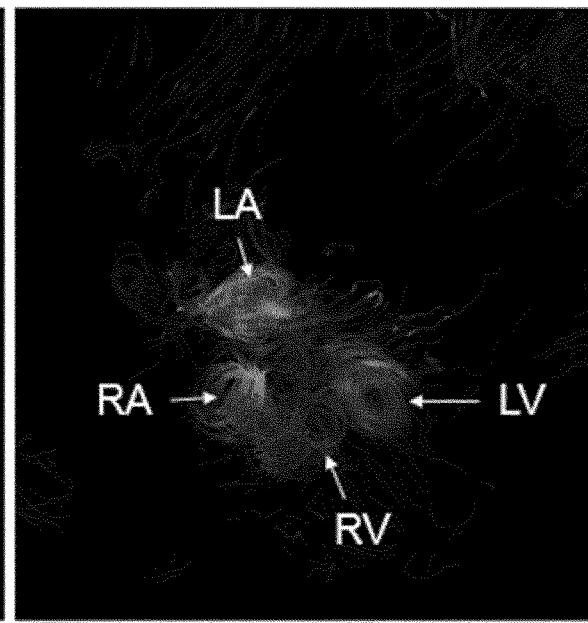
Figure 14:
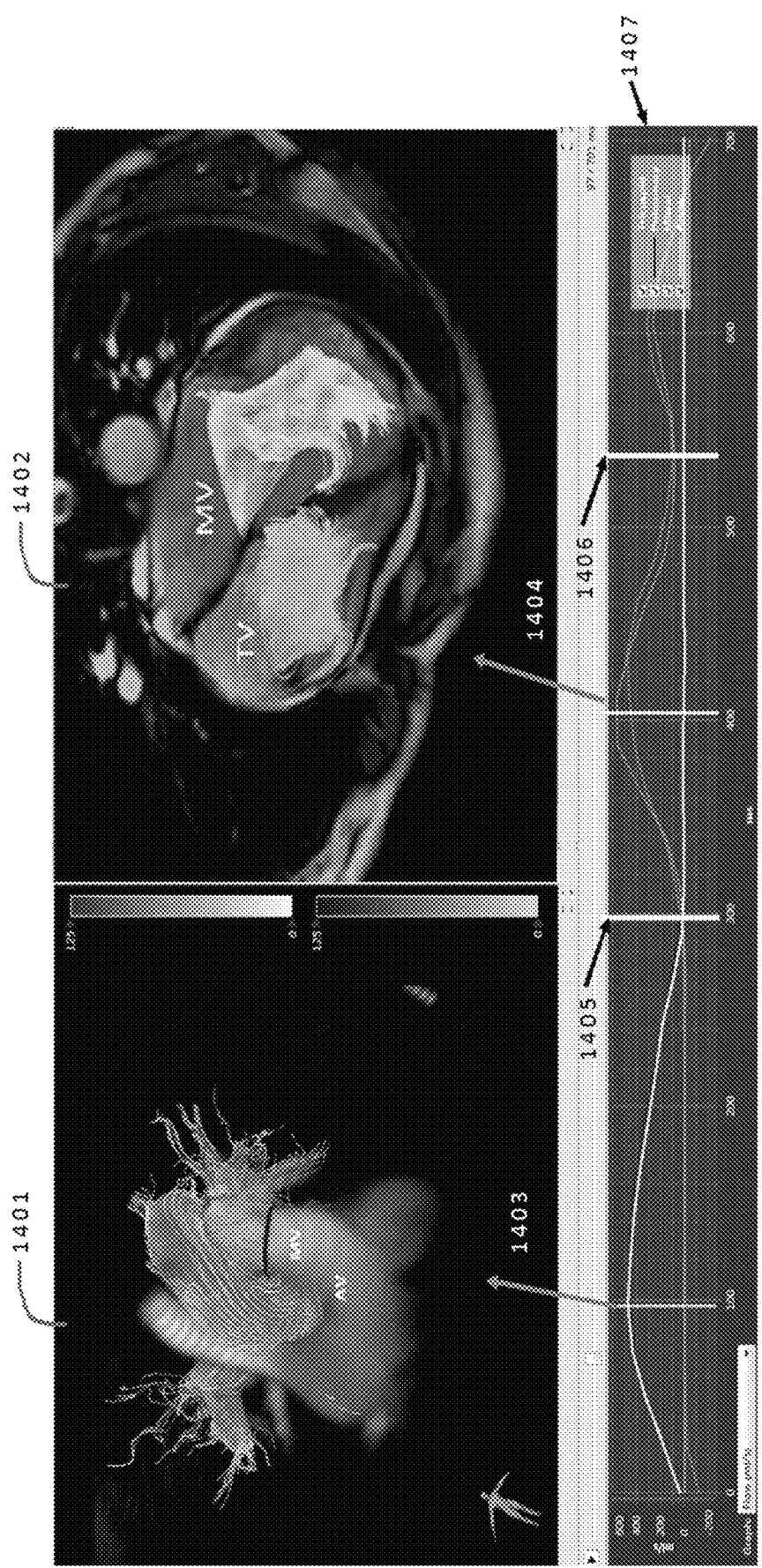
FIG. 14 shows the streamlines superimposed on a rendered volume of the 4D MR Flow at two cardiac phases, as well as the blood flow through the four valves.

For further explanation of the automatic localization of the valve(s) by means of the 4D MR Flow dataset, reference is made to FIG. 13*a*, FIG. 13*b* and FIG. 14. FIG. 13*a* and FIG. 13*b* corresponds to the same dataset and the visualization is performed in the same perspective (viewing direction). FIG. 13*a* shows a volume rendered view of the 4D MR Flow dataset. The volume rendering can for example be performed based on the static volume as described before within step 102*b*. Within FIG. 13*a*, the heart chambers are roughly identified by sketching (right atrium (RA), left atrium (LA), right ventricle (RV), left ventricle (LV)) and the main arteries are designated. As mentioned before, a 4D MR Flow acquisition consists of time resolved three-dimensional phase contrast MRI. This means that a 4D MR Flow datasets consists of 3D volumetric velocity and 3D volumetric anatomical (magnitude) data at several time moments (phases) within the cardiac cycle. For each separate phase, the trigger time with respect to the r-top of the ECG signal is known. This information can for instance be obtained through the "headers" of the conventional DICOM file format.

FIG. 14 shows the blood flow through the four valves (1407). At peak systole (1403), the flow through the aortic valve and pulmonary valve is at maximum as shown by image 1401. During diastole at peak ventricular filling (1404), the flow through the mitral valve and tricuspid valve is at maximum as shown by image 1402. Both moments in the cardiac cycle, the streamlines are visualized in FIG. 13b by picture 1301 and 1303. FIG. 13b shows the streamlines within the 3D volume at different phases within the cardiac cycle. Streamlines is a line plotted through in a flow field at a given instant in time such that it is aligned with the local velocity vectors at all points along its length (Buonocore M H, "*Visualizing blood flow patterns using streamlines, arrows, and particle paths*", Magn Reson Med 1998; 40:210-226). Within FIG. 13b the brightness of the streamlines indicates the local blood velocity. The brighter (whiter) the streamline, the higher the velocity at that position. To optimize the streamline calculation for current task, the information from the magnitude data can be used. For instance, weighting the local velocities with the intensity from the magnitude data at the investigation spatial location. By this, incorrect velocities information within the 4D MR Flow dataset, for instance due to noise in the imaging or due to artefacts caused by air in the lungs, can be ignored, since the heart and the vessels will have different pixel intensities in the magnitude data than for instance lung tissue. Another approach to optimize the streamline calculation is by first segmenting the cardiac structures (heart chambers and large vessels such as aorta, pulmonary) as explained further within step 1102, and weight the velocity based on the segmentation outcome, for instance low weight outside segmentation region and high weight inside segmentation region.

Within FIG. 13b, picture 1301 corresponds with the cardiac phase labelled by 1403 in FIG. 14. Picture 1302 corresponds with the cardiac phase labelled by 1405. Picture 1303 corresponds with the cardiac phase labelled by 1404 and picture 1304 corresponds with the cardiac phase labelled by 1406. Note that within FIG. 14, only the flow through the valves is visualized by means of streamlines. Picture 1401 shows the flow through aortic valve and pulmonary valve and picture 1402 shows flow through tricuspid and mitral valve.

At the start of the systolic phase, the blood is pumped from the left and right ventricle into the aortic artery and the pulmonary artery respectively. This results in a major acceleration of the stationary blood from the ventricles into the aorta- and pulmonary artery and also the blood in these arteries is accelerated from nearly zero flow. The aortic artery and the pulmonary artery are large vessels and can be assumed as cylindrical shaped objects. The acceleration of the blood and the consequently increase in the blood velocity including the presumed cylindrical shape can be detected within the 4D MR Flow dataset (FIG. 13b, 1301). The aorta (1305) and pulmonary artery (1306) are clearly visible, and the arrows (1311) mark the blood flow direction. The detection of these cylindrical shapes can be for instance performed by deploying vesselness image processing techniques as for example thought by Staring M. et al, DPS, "*Pulmonary Vessel Segmentation using Vessel Enhancement Filters*", VESSEL12 Challenge of ISBI Conference. 2012; p. 1-8. After detecting both the aortic artery and pulmonary artery, the valve location is determined by tracking the blood flow backwards (back to ventricles) in both arteries. The aortic valve and the pulmonary valve location are determined at the transition of the ventricular volume and artery. This transition is identified as the last location (looking from arteries, so in opposite direction as the arrows 1311), in which flow is identified in one direction only during systole. The ventricles can be optionally segmented by the approach as explained further within step 1102. Another approach to localize the aortic valve and pulmonary valve is by for instance combining the information at peak systole (1301) and at end-systole 1302). At end-systole (1302), the aorta and pulmonary valve just closed, but the flow in aorta and pulmonary is not fully zero. This transition is identified by 1307 and 1308, representing the aortic valve and pulmonary valve respectively.

After the systolic phase the aortic valve and the pulmonary valve closes and the mitral valve and the tricuspid valve opens. This results in rapid filling of the ventricles with blood from the atria's as can be seen in FIG. 13b, 1303. A major blood volume flows from the atrial chamber to the ventricle chamber through the valve opening. The valve opening is much smaller with respect to the atrial volume and the ventricular chamber. The moment the mitral valve or tricuspid valve opens, the blood in the atria starts to accelerate and reaches a maximum velocity during the passage through the heart valves and the blood velocity will decelerate in the ventricles. The rapid ventricular filling results in a local concentrated high blood flow velocity in the valvular opening as shown by 1309 and 1310, representing the mitral valve and tricuspid valve respectively. The locations of the concentrated high velocities can be detected in the 4D MR Flow data. The mitral valve and tricuspid valve location are determined at the center of the detected high velocity locations.

For all above described approaches for determining the valve location within step 1101, the information obtained from FIG. 13b, picture 1304 can be used additionally. Picture 1304 represents the phase just after ventricular filling and just before arterial contraction phase. At this moment within the cardiac cycle, all chambers can be easily identified and this information can be used to guide the valve localization. Optionally, the information obtained within every phase can be used for the valve localization.

The method as described in step 1101 is based by using streamlines which are derived from the 4D MR Flow dataset as an illustration example. The method of step 1101 is not restricted to a streamlines approach. In fact, the method of step 1101 utilizes the difference in flow behavior, accelerations and flow dynamics within the heart during the cardiac cycle and different 4D flow quantification techniques can be used. Such as instantaneous streamlines, pathlines, particle tracing, kinetic energy, turbulent kinetic energy, vorticity, etc.

Figure 11:
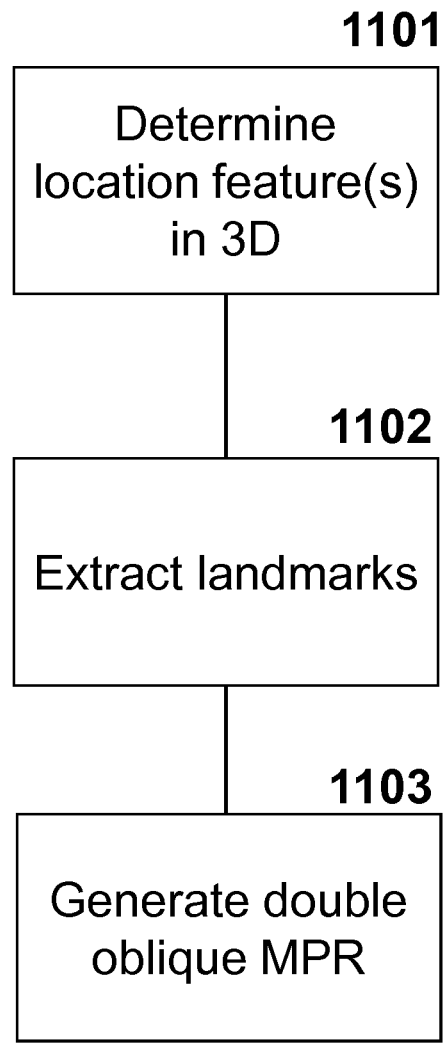
FIG. 11 shows a flowchart of the steps for generating optimal 2D long axis cine images is automatically.
Figure 15A:
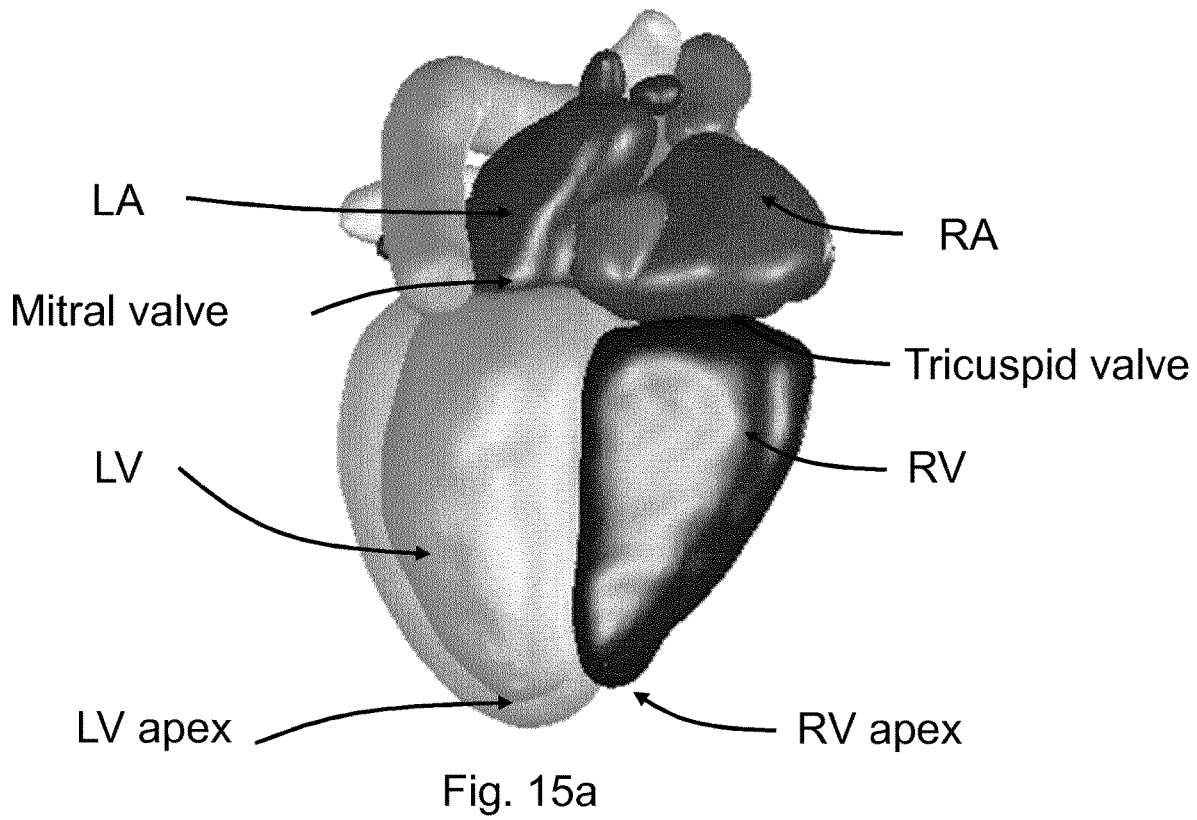
FIGS. 15a, 15b and 15c shows a generic 3D anatomical surface model of the heart with annotated features.
Figure 15B:
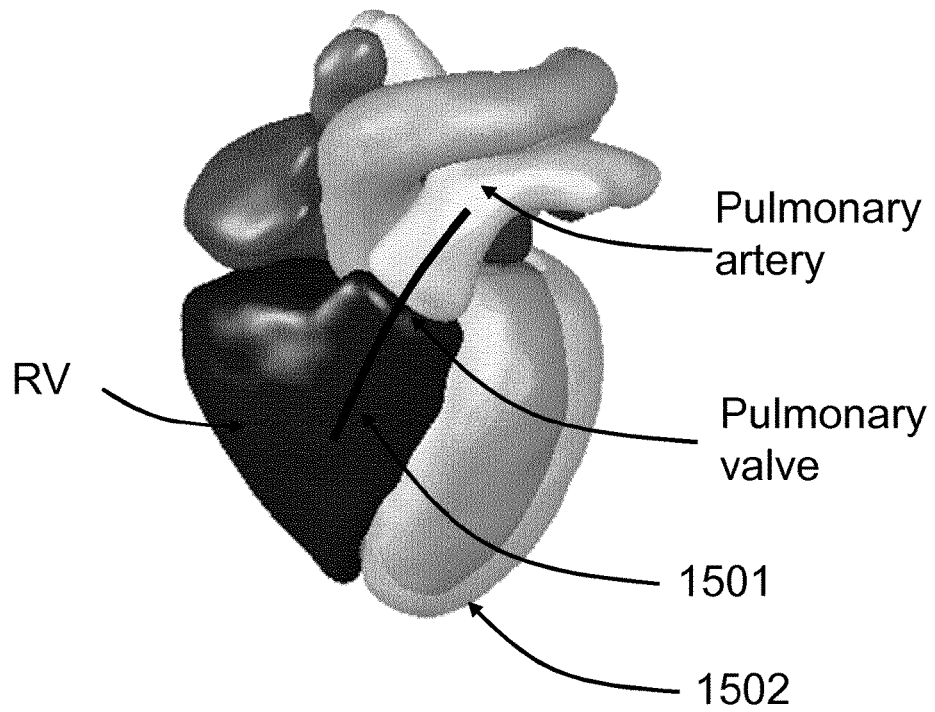
Figure 15C:
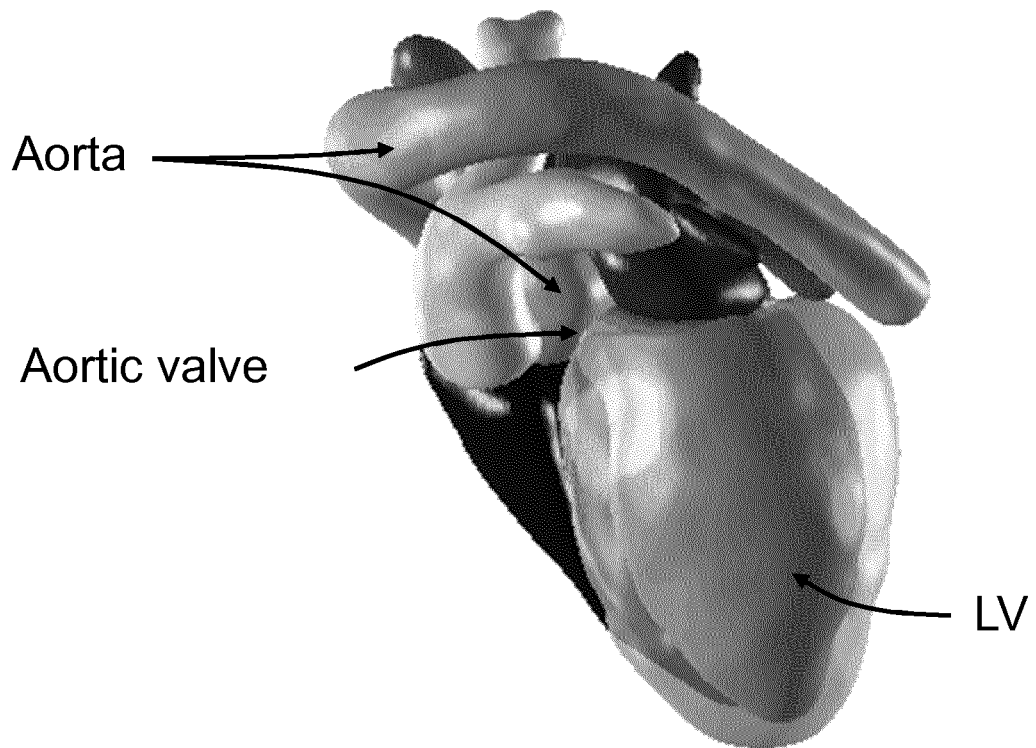
Figure 22:
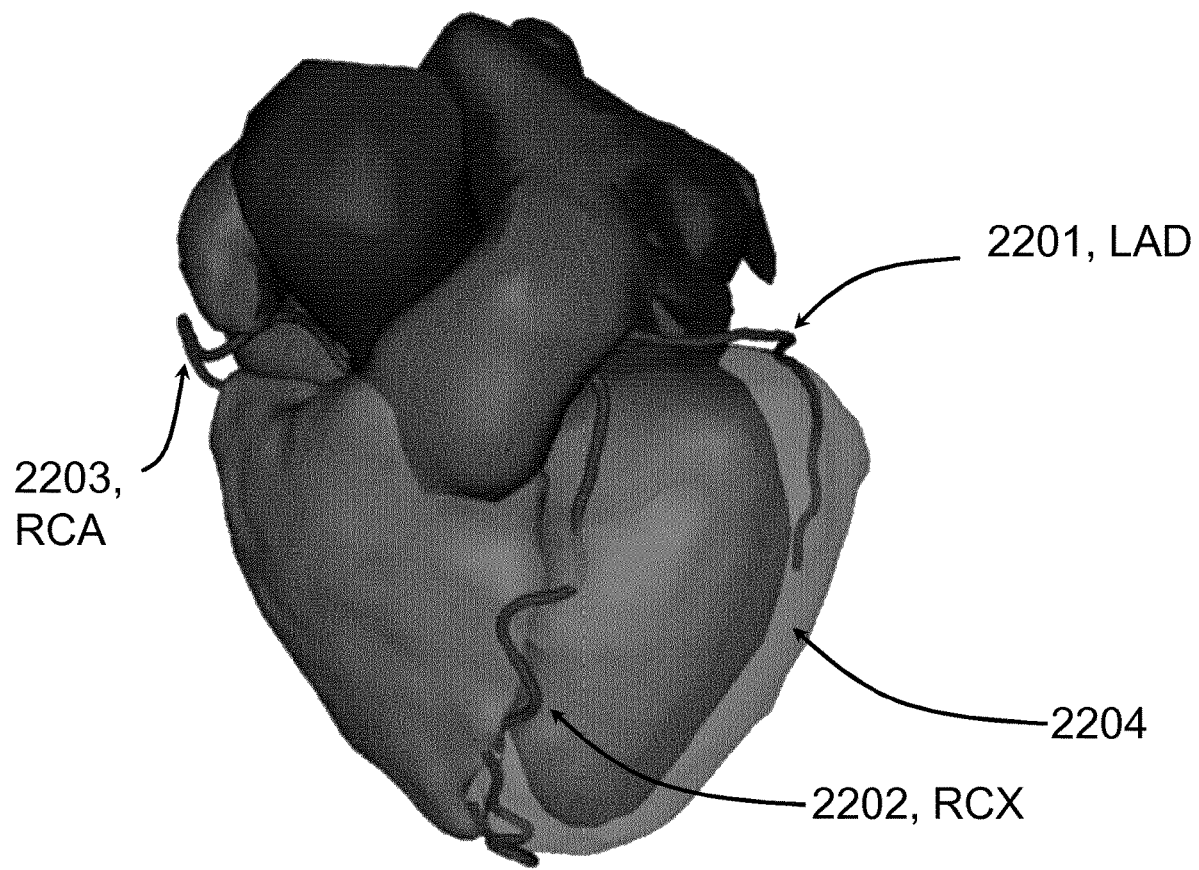
FIG. 22 shows the main coronary arteries in relation to a generic heart model.
Figure 23A:
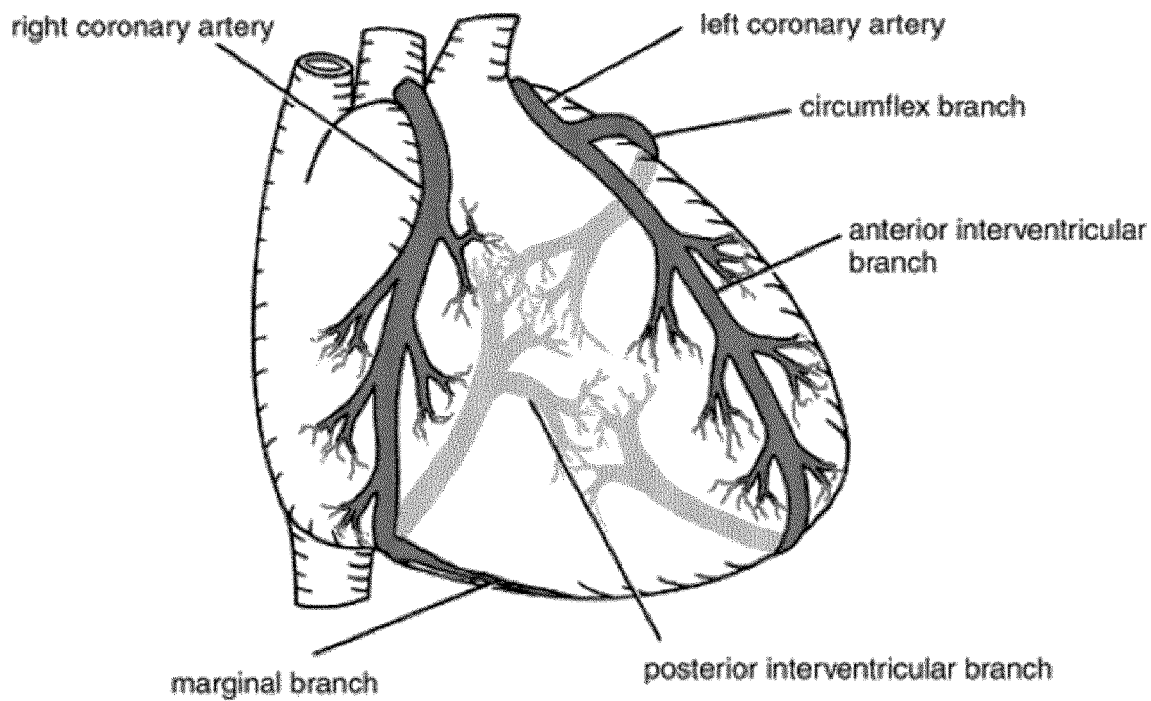
FIG. 23a shows the main coronary arteries in relation to the heart.

Step 1102 from FIG. 11 describes a feature extraction process, which is used by step 1103 and optionally by step 1104. To extract the relevant features, for instance to generate the 2D long axis cine images by step 1103 and 1104, a generic 3D anatomical surface model with annotated features as seen in FIGS. 15a, 15b and 15c can be used. FIGS. 15a, 15b and 15c, shows the same 3D anatomical surface model, but visualized at different perspectives to allow clear illustration of the relevant features. For instance in FIG. 15a, all ventricles and atria's are clearly visible as well as the ventricle apex locations. Furthermore, the location of the mitral valve and tricuspid valve are clearly visible. FIG. 15b shows a perspective in which the right ventricle, pulmonary valve and pulmonary artery are clearly visible and FIG. 15c a perspective with clear view on the left ventricle, aortic valve and aorta. The generic 3D anatomical surface model may include coronary arteries and coronary veins as show by FIG. 22, FIG. 23a and FIG. 23b. Multiple models may be generated allowing difference in coronary dominance. If e.g. the right coronary artery is the main supplier of the posterior descending artery, it is said that the patient has a right coronary dominance heart type. Likewise, a left coronary dominance heart type or balanced heart type are defined.

The 3D anatomical surface model can for instance be generated as an average model from multiple computed tomography and/or MRI scans of the heart or be retrieved from an atlas database as for instance described by Metz et al, "*Regression-based cardiac motion prediction from single-phase CTA*", IEEE Transactions on Medical Imaging 31; 311-1325, or by Zhuang, "*Challenges and methodologies of fully automatic whole heart segmentation: a review*", Journal of Healthcare Engineering 2013; 4(3):371-408). The 3D anatomical surface model is then registered to the 4D MR Flow dataset for the corresponding heart phase as for instance described by Crum et al, "*Non-rigid image registration: theory and practice*", The British Journal of Radiology; 77 (2004), S140-S153, or by Zhuang et al, "*A Registration-Based Propagation Framework for Automatic Whole Heart Segmentation of Cardiac MRI*", IEEE Transaction on Medical Imaging 2010 September; 29(9):1612-25. After the registration process, it is known where the relevant features (e.g. valves, valve annulus, ventricles, atriums, the apexes, etc.) are located in the volumetric data of the 4D MR Flow dataset. Optionally the anatomical model that is fitted can also be 4D (3D+time). This to allow improved compensation for heart motion.

Optionally, the 3D velocity information present in the 4D MR Flow dataset may be optimized, since the 3D velocity information within the 4D MR Flow dataset may be affected by acquisition noise, flow artifacts, and resolution limits. After the registration process the 3D anatomical model is aligned with the patient specific geometry as obtained from the 4D MR Flow dataset. This allows reconstruction of noise-free, flow artifact-free, high-resolution 3D velocity fields by merging 4D MR Flow with computational fluid dynamics as for instance thought by Bakhshinejad et al, "*Merging computational fluid dynamics and 4D Flow MRI using proper orthogonal decomposition and ridge regression*", Journal of Biomechanics 2017 Jun. 14; 58:162-173 or by Rispoli et al, "*Computational fluid dynamics simulations of blood flow regularized by 3d phase contrast mri*", Biomedical Engineering 2015; Online; 14(1):110. Reconstruction noise-free, flow artifact-free, high-resolution 3D velocity fields will benefit further quantification, especially for pressure based calculation or wall shear stress. Optionally, the step as described in 1101 may be performed again based on the optimized 3D velocity information. The reconstruction noise-free, flow artifact-free, high-resolution 3D velocity fields, or optimized 3D velocity information is derived from the 4D MR Flow dataset as described above and will be considered part of the data when referring to 4D MR Flow dataset.

Within step 1103 the 2D long axis cine images can then be then generated based on double oblique multi planar reconstruction as described in the explanation of the manual method (step 102a) but now by using the automatically identified features to automatically identify the reference lines, instead of the user positioned reference lines. For instance, to generate multiple L2CH view, a reference lines between the LV apex and center of mitral valve is generated allowing double oblique reconstructions which are rotated along this line (see also FIG. 10). This method also allows curved multi planar reconstructions. For instance, the 2D long axis cine image, in which the pulmonary valve can be tracked optimal, can be generated along a curved reference line that goes through the center of the pulmonary valve and following the center of the pulmonary artery and the RV connecting the pulmonary artery (see FIG. 15b, 1501). Now by multi planar reconstructions, which are rotated (perpendicular) along this curved reference line, multiple 2D long axis cine views optimal for pulmonary valve tracking can be generated.

Alternatively, the 2D long axis cine images can be generated based on double oblique multi planar reconstruction as described in the explanation of the 3D approach as described within the semi automatic method (step 102b). Within step 1104, the 3D point (FIG. 9, 901) as described in the 3D approach, is now the derived valve position within step 1101 or optionally optimized by step 1102. The remaining steps to generate the 2D long axis cine images are as described by the 3D approach within the semi automatic method (step 102b).

The generated 2D long axis cine images can be further used for instance, for the valve determination (step 103 of FIG. 1). However, these 2D long axis cine images can also be used for other analysis purposes. For instance, left atrium and/or right atrium segmentation and analysis, left ventricle and/or right ventricle segmentation, wall thickness, wall motion, end-diastolic and/or end-systolic volume determination, ejection fraction and the like.

Step 103: Localize Valves in 2D

In the generated 2D long axis cine views, the valve is localized. This can be done manually, semi-automatically or automatically as shown in step 103 of FIG. 1.

Manual Localize Valves in 2D Long Axis Cine Images (103a)

Figure 16A:
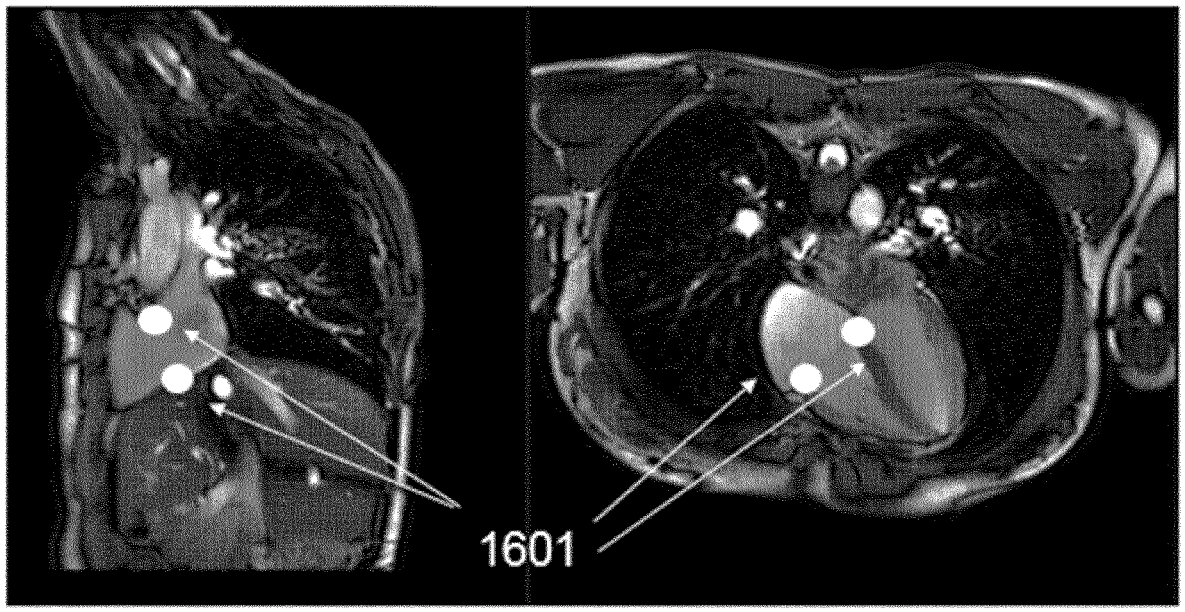
FIGS. 16a and 16b shows manual annotation of the valves in long axis images.
Figure 16A:
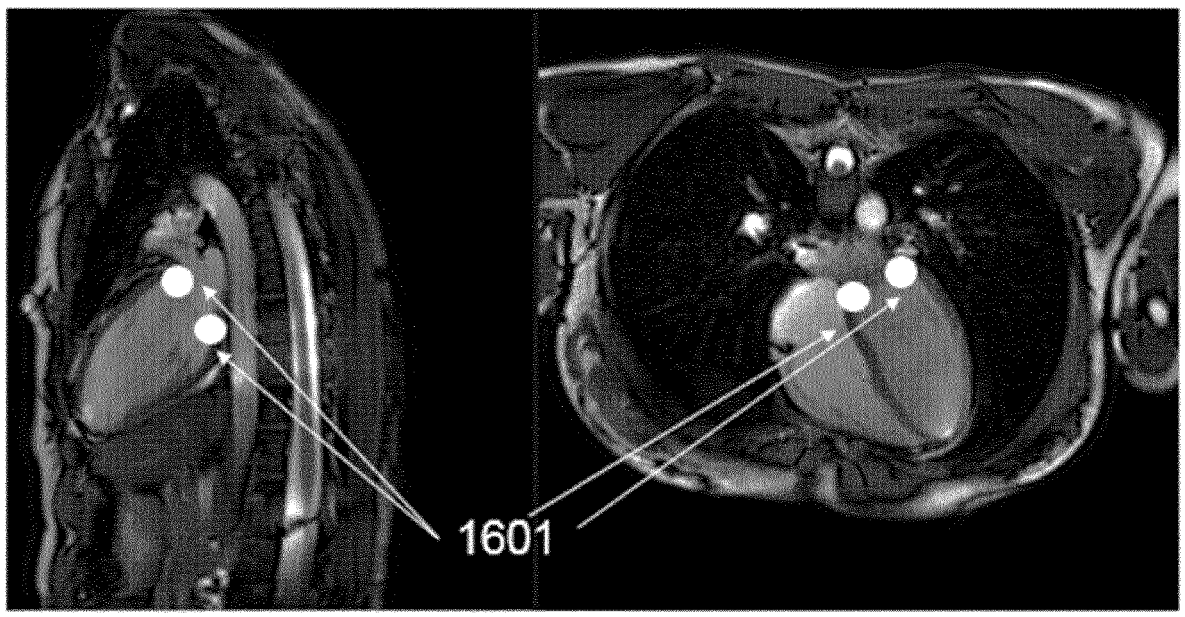
Figure 16B:
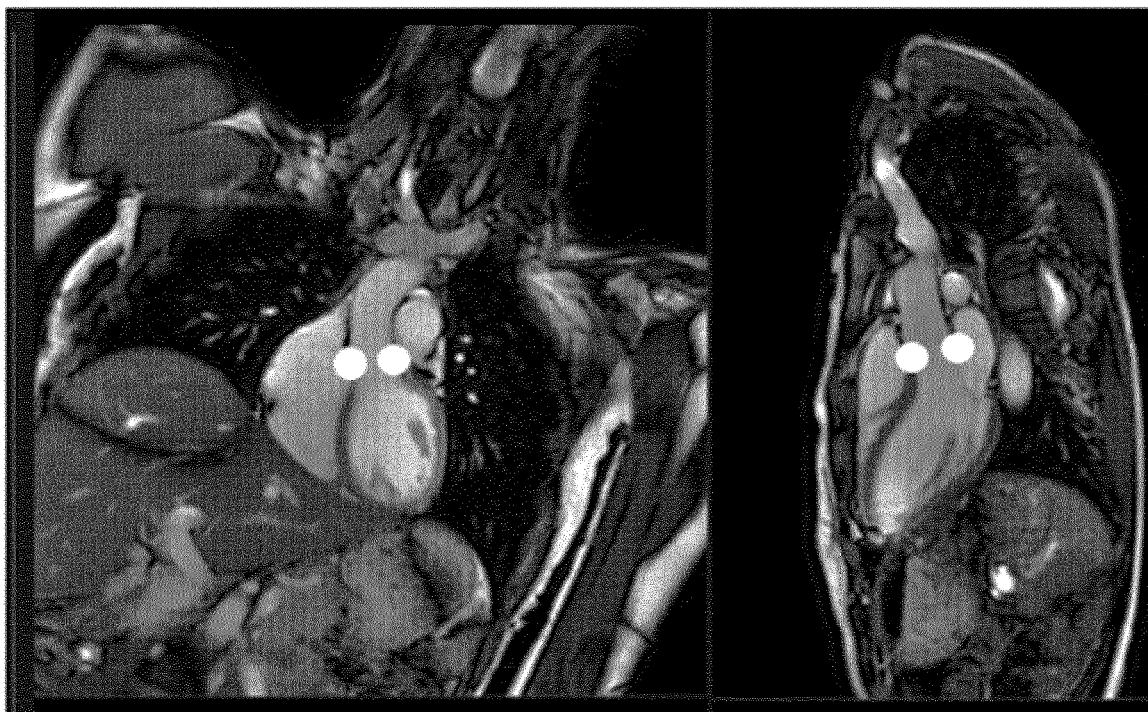
Figure 16B:
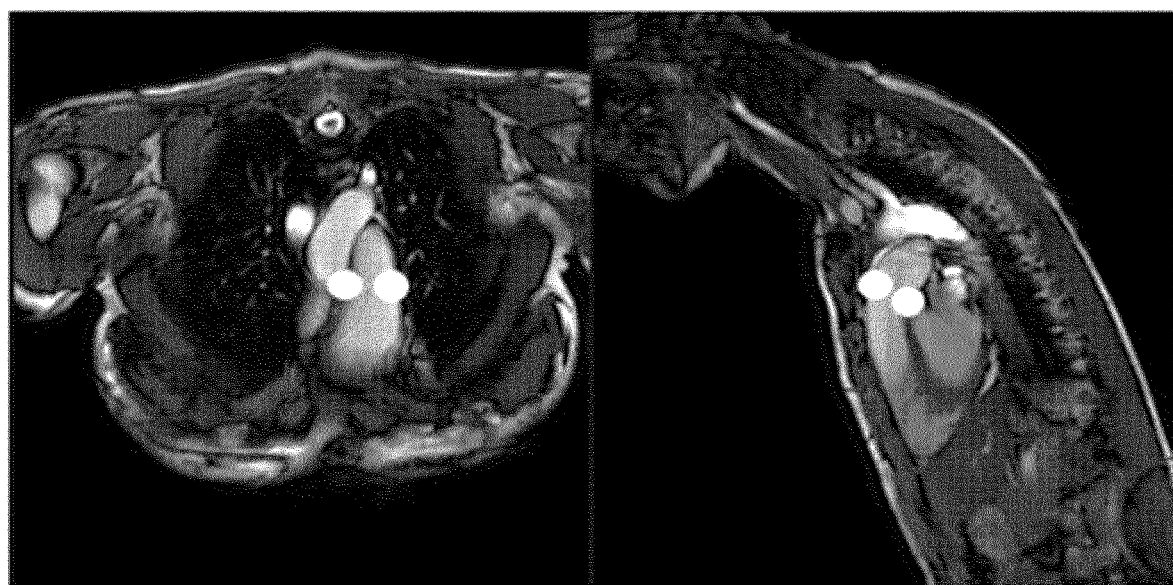

Within the generated 2D long axis cine view(s), one or multiple valves can be manually identified. In this case, the user indicates the precise location of one or multiple valves in the generated 2D long axis cine images as can be seen in FIG. 16a and FIG. 16b. For example, within FIG. 16a the user can identify the tricuspid valve and mitral valve as shown by the white dots (1601) within the optimal 2D long axis cine view. FIG. 16b shows the same, but now for the aortic valve and pulmonary valve.

Semi-Automatic Localize Valves in 2D Long Axis Cine Images (103b)

In the semi-automatic approach, the initial valve position(s) are determined according to the automatic method of step 102c (based on velocity data or based on a generic 3D anatomical surface model with annotated features) as described by step 1101 and followed by the optional step 1102 in more detail. Based on these steps, the detected location of one or multiple valves are shown in the generated 2D long axis cine images. The user can then optimize the position of the valve if necessary.

Automatic Localize Valves in 2D Long Axis Cine Images (103c)

The valves can be determined fully automatically in the generated 2D long axis cine images based on the annotated valve position within the registered generic 3D anatomical surface model as described before (step 1101, 1102).

Another method to localize the valve(s) is by use of machine learning algorithm. Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs. Machine-learning is employed in a range of computing tasks where designing and programming explicit algorithms is infeasible. Machine-learning algorithms are widely used for processing of natural images (LeCun et al, "*Deep learning*", Nature 521 (7553) (2015), p 436-444) and since recently also in medical image analysis for classification and segmentation tasks, as for example provided by Wolterink et al, "*Automatic coronary artery calcium scoring in cardiac ct angiography using paired convolutional neural networks*", Medical Image Analysis 2016, p 123-136.

Given a dataset of images (e.g. the longitudinal cine MRI) with known class labels (e.g. location of the valve(s) within these longitudinal cine MRI), machine-learning system can predict the class labels of new images. There are at least two parts to any such system. The first part of the machine-learning is a feature extraction (extractor), being an algorithm for creating a feature vector given an image. A feature vector comprises a series of factors (e.g. multiple numbers) that are measured or extracted from the image dataset(s), which describe or characterize the nature of the object of interest, in our case the valve(s) of the heart. These features are then used by the second part of the system, a classifier, to classify unseen feature vectors extracted from the unseen image. Given a (large) database of images and extracted feature vectors whose labels are known and were used beforehand to train the machine-learning algorithm, classifying unseen images based on the features extracted the same way as in images with (known) labels (training images) is possible.

The features characterizing the valve(s) are extracted from the generated long axis cine views. For this, any engineered characteristic that describes the valve(s) texture (e.g. Gaussian, Haralick texture features) can be used. Also, valve(s) features as extracted by means of encoding methods such as convolution auto-encoder can be used. Any combination of these features can be selected. Convolutional autoencoder (CAE) is a technique for extracting features from image data. The aim of an auto-encoder is to learn a representation (encoding) for a set of data, typically for the purpose of dimensionality reduction. An auto-encoder is based on the encoder-decoder paradigm, where an input is first transformed into a typically lower-dimensional space (encoder part) and then expanded to reproduce the initial data (decoder part). It is trained in supervised or unsupervised fashion allowing it to extract generally useful features from unlabeled data, to detect and remove input redundancies and to present essential aspects of analyzing data in robust and discriminative representations. A CAE compress all the data from an image to a small vector from which it must contain enough information to reconstruct the image by the decoder. By this, the encoder is forced to learn features about the image being compressed. This method can also be used to replace step 1101 and 1102.

Step 104: 2D/3D Tracking

When the valve position(s) have been determined in the 2D long axis cine images as described in step 103 of FIG. 1, the valve motion during the cardiac cycle can be tracked. This tracking can be done directly on the generated long axis cine images (2D long axis cine images) or on the volumetric 4D MR Flow image set.

The valve motion during the cardiac cycle can be followed in the generated 2D long axis cine images of step 102 of FIG. 1, using for instance template matching approaches as described by Maffessanti et al "*Three-dimensional dynamic assessment of tricuspid and mitral annuli using cardiovascular magnetic resonance*", European Heart Journal—Cardiovascular Imaging (2013) 14, 986-995 or by using for instance the method described by Dewan et al, "*Deformable motion tracking of cardiac structures (DE-MOTRACS) for improved MR imaging*", Computer Vision and Pattern Recognition, 2001, p 1-8.

In both methods the valve landmarks are appointed (marked) in a single image frame (step 103), either manual (103*a*), semi-automatic (103*b*) or automatic (103*c*). At the marked locations, an image template is created with a fixed size. This image template is matched with a reference template. This reference template is obtained in two different manners as described by Maffessanti and Dewan. Another improvement would be to dynamically adjust the template size during the tracking process.

The method of Dewan makes use of a multiple template matching approach where the reference templates are available in a template database. Using multiple templates makes the method less sensitive for noise and acquisition artifacts. The valve tracking will take place by registration of the 2D long axis cine images templates per time frame with the multiple templates stored in the database.

Another method to track the valve is by means of image registration techniques for instance as thought by Bo Li et al, "*Automatic tracking of mitral valve motion by non-rigid image registration*", Journal of Cardiovascular Magnetic Resonance 2008, Volume 10 supplement 1. The positions of the valve(s) as localized in step 103, can also be translated to their 3D positions as the location of the 2D long axis cine images in the volumetric data is known. Using this 3D position of the valve(s), 3D tracking can be performed as described in step 107.

Alternatively, the valve motion can be tracked by manual identification. In this situation, the user indicates the precise location of one or multiple valves in all phases within the generated 2D long axis cine images.

The location of the valve(s) should preferable be tracked (within the 2D long axis cine images) in at least all successive images (phases) which represents one cardiac cycle.

Step 105: Feedback 2D/3D Tracking

Figure 17:
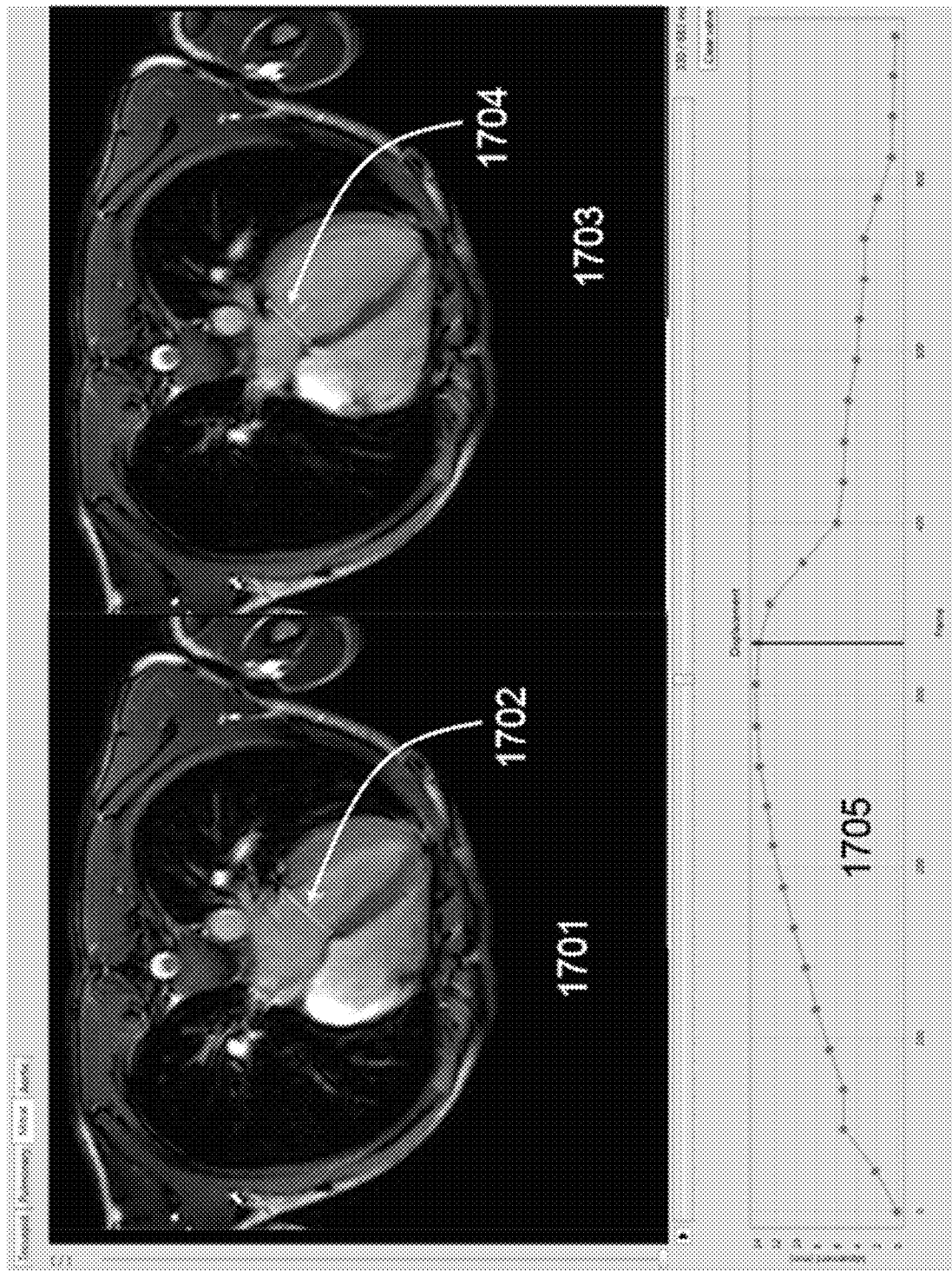
FIG. 17 shows an example of visual feedback of the valve tracking process based on 2D long axis cine images.

Once the valve(s) have been tracked, the results can be shown to the user. FIG. 17 provides an example of visual feedback of the valve tracking process based on 2D long axis cine images, and a mitral valve tracking example is provided. Picture 1701 within FIG. 14 represents a frame of the 4CH cine view at the end-systolic cardiac phase, and 1702 present the tracked valve location within this end-systolic frame. The same is shown during an end-diastolic frame by picture 1703 and with the tracked valve position 1704. In case the tracking is incorrect, the user can reposition the valve location and optimally reinitiate the valve tracking process (as described in step 104 of FIG. 1).

Furthermore, the user can then for instance reposition a valve plane in the event the tracking was not correct. The corrected valve plane can then, for instance be used, to generate new 2D long axis cine images or short axis views and reinitiate the valve tracking process (as described in step 104 of FIG. 1).

Based on the tracked valve, quantitative analysis can be performed to assess valve dynamics. For instance, the valve motion can be quantified by computing the displacement perpendicular to the tracked valve plane which can be visualized as a displacement graph as shown by 1705 in FIG. 17. The calculated valve motion also allows for automatic correction of through plane motion during the reformatting step (FIG. 1, step 111).

Other quantitative analysis results based on the tracked valve can for instance be related to the assessment of valve tilting during the cardiac cycle or within specific part(s) of the cardiac cycle or to assess valve deformation by quantifying the change in valve annulus shape during the cardiac cycle.

Step 106: Localize Valves in 3D

The valve(s) localization in 3D can be performed by the method(s) described in step 102*c* (i.e. by step 1101 and/or 1102) or 103*c*.

Another method to localize the valve(s) in 3D is by means of machine learning for instance as thought by B. D. de Vos et al, "*ConvNet-Based Localization of Anatomical Structures in 3D Medical Images*", IEEE Transactions on Medical Imaging, 2017, vol. PP, pp. 1-1.

Step 107: 3D Tracking

When the valve position(s) (valve features) have been determined as described in step 106 of FIG. 1, the valve motion during the cardiac cycle can be tracked. In our 3D valve tracking approach, the idea of multiple template matching as described in step 104 is adopted from Dewan and combined with the idea of using reference templates of the 4D MR Flow data set instead of reference templates in a data base from Maffessanti. The presented template matching methods of Dewan and Maffesanti are only applied to the 2D long axis cine images. These 2D long axis cine images are restricted to two dimensions, for the 4D MR Flow image dataset however, the approach can be extended to the third dimension.

Figure 18A:
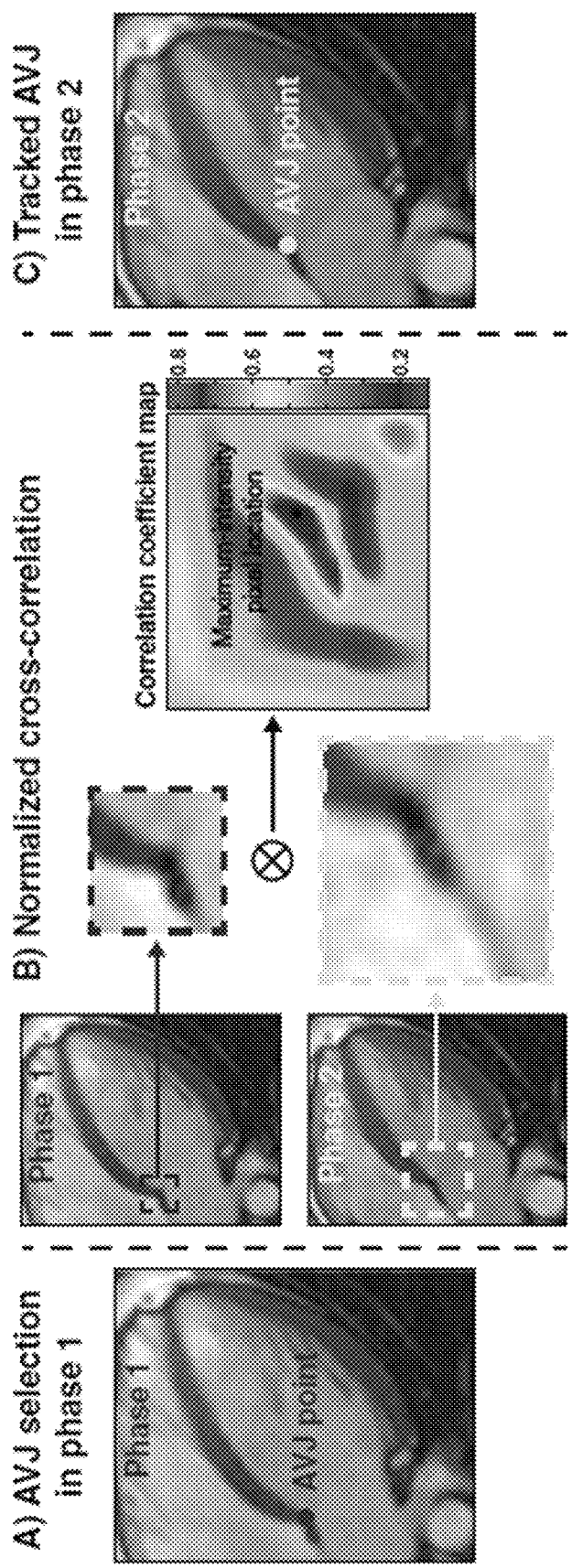
FIG. 18a shows a schematic representation of the cross correlation between successive phases.
Figure 18B:
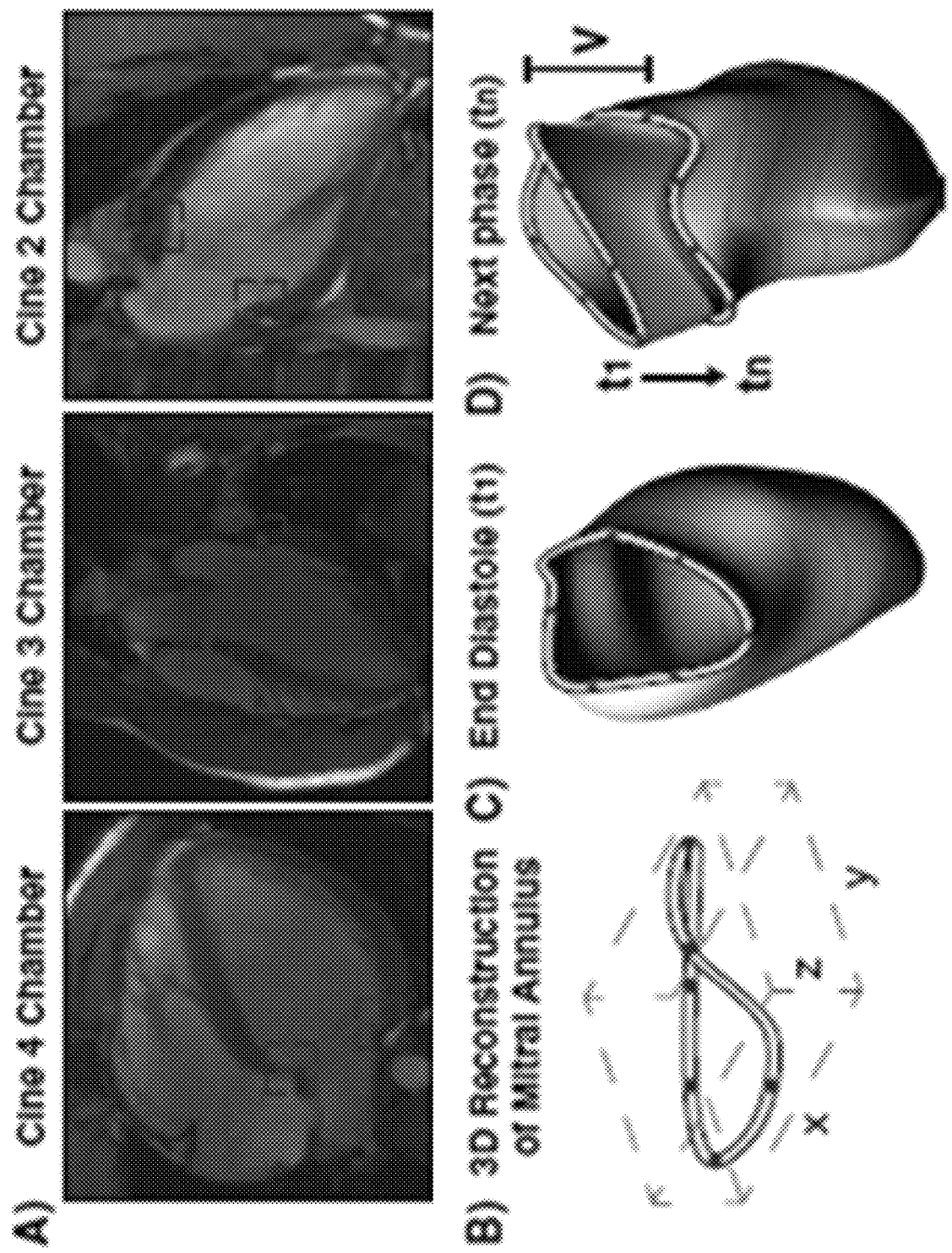
FIG. 18b shows the tracking of multiple valve features for the mitral valve.

This results in a template matching approach in which the templates are no longer two dimensional images but become three dimensional volumetric image features. The size of the templates is not fixed, but is adapted to the image acquisition resolution and optionally dynamic adjust the template size during the tracking process. Template matching can be performed, for instance, by use of normalized cross correlation as illustrated in FIG. 18. FIG. 18*a* shows the basic steps of normalized cross correlation feature tracking, in FIG. 18*a* (plane A) a feature of a valve location is shown, in this example the atrium-ventricular junction (AVJ) point. Plane B of FIG. 18*a* shows a schematic representation of the cross correlation between successive phases (phase1 and phase2). The correlation coefficient map shows the probability of the new location (in phase 2) of the tracked feature. Plane C of FIG. 18*a*, shows the new position in phase 2 of the tracked feature (AVJ point). The illustration in FIG. 18*a*, is presented in 2D to allow easy presentation. As mentioned before, the template matching is performed in 3D, which might be better illustrated by FIG. 18*b*. FIG. 18*b* shows the tracking of multiple valve features (six features in the picture of plane A FIG. 18*b*) for the mitral valve. Plane B of FIG. 18*b* shows a 3D reconstruction of the tracked valve, in this example the mitral annulus. Plane C of FIG. 18*b* shows the location of the tracked mitral valve with respect to the left ventricle at two different phases within the cardiac cycle (end diastole and next phase).

Another method for 3D valve tracking is through the use of isosurfacing as described in Ji et al, "*Volume tracking using higher dimensional isosurfacing*", IEEE Visualization, 2003. This method tracks time varying isosurfaces and interval volumes using higher dimensional isosurfaces. Local features are defined as connected isosurfaces or interval volume components, and are tracked by propagating and interactively slicing the isosurface or interval volume. Another method to track the valve in 3D is by means of non-rigid image registration techniques, for instance as thought by Bo Li et al, "*Automatic tracking of mitral valve motion by non-rigid image registration*", Journal of Cardiovascular Magnetic Resonance 2008, Volume 10 supplement 1.

Step 108: Feedback 3D Tracking

Once the valves have been tracked, the results can be shown to the user. For instance, the results can be presented in 2D long axis cine images as described in step 1103 or 1104. The user can then for instance reposition one or multiple valve location(s) in the event the tracking was not correct. The corrected valve location can then for instance be used to generate new 2D long axis cine images or short axis views. Based on the generated 2D long axis cine images, the valve localization as described in step 103*a* and 103*b* can be performed as well.

In addition, the valve motion can be quantified as explained within step 105 of FIG. 1.

Step 109: Create Valve Plane

Once the at least one valve has been tracked in the 4D MR Flow data and optionally feedback has been provided by the user, for every time moment a spatial orientation and position of the valve plane can be derived.

If the user only defined valve landmarks in one 2D long axis cine image sequence, for each phase the resulting 3D planes are completely defined by the vector between the 3D positions of the valve landmarks (converted from the 2D long axis cine image coordinates) and a vector perpendicular to the 2D long axis cine image (cross-product of the 2D long axis cine image orientation vectors). The resulting 3D valve planes will therefore always be perpendicular to the 2D long axis cine images. The average of the two 3D valve landmark positions is taken as the center position of the valve plane per phase.

If the user defined valve landmarks on two or more 2D long axis cine image sequences, then for each time frame a 3D plane is fitted through the valve landmarks in 3D (again converted 2D long axis cine image coordinates) using Single Value Decomposition (least squares fit). The center of the aligned bounding box of the valve plane projected 3D landmark points (aligned to the larger of the two vectors between the projected valve landmarks) is used as the center position of the valve plane per phase.

Optionally, if the user defined valve landmarks on two or more 2D long axis cine images, the plane can be generated as a curved plane for instance by non-uniform rational B-spline surface fitting.

Step 110: Plane Optimization

The plane orientation is optionally optimized to preserve its perpendicularity to the blood flow (step 110 of FIG. 1), following the method described in Calkoen et al., "*Characterization and Improved Quantification of Left Ventricular Inflow Using Streamline Visualization With 4D Flow MRI in Healthy Controls and Patients After Atrioventricular Septal Defect Correction*", Journal of Magnetic Resonance Imaging (2014).

Figure 19:
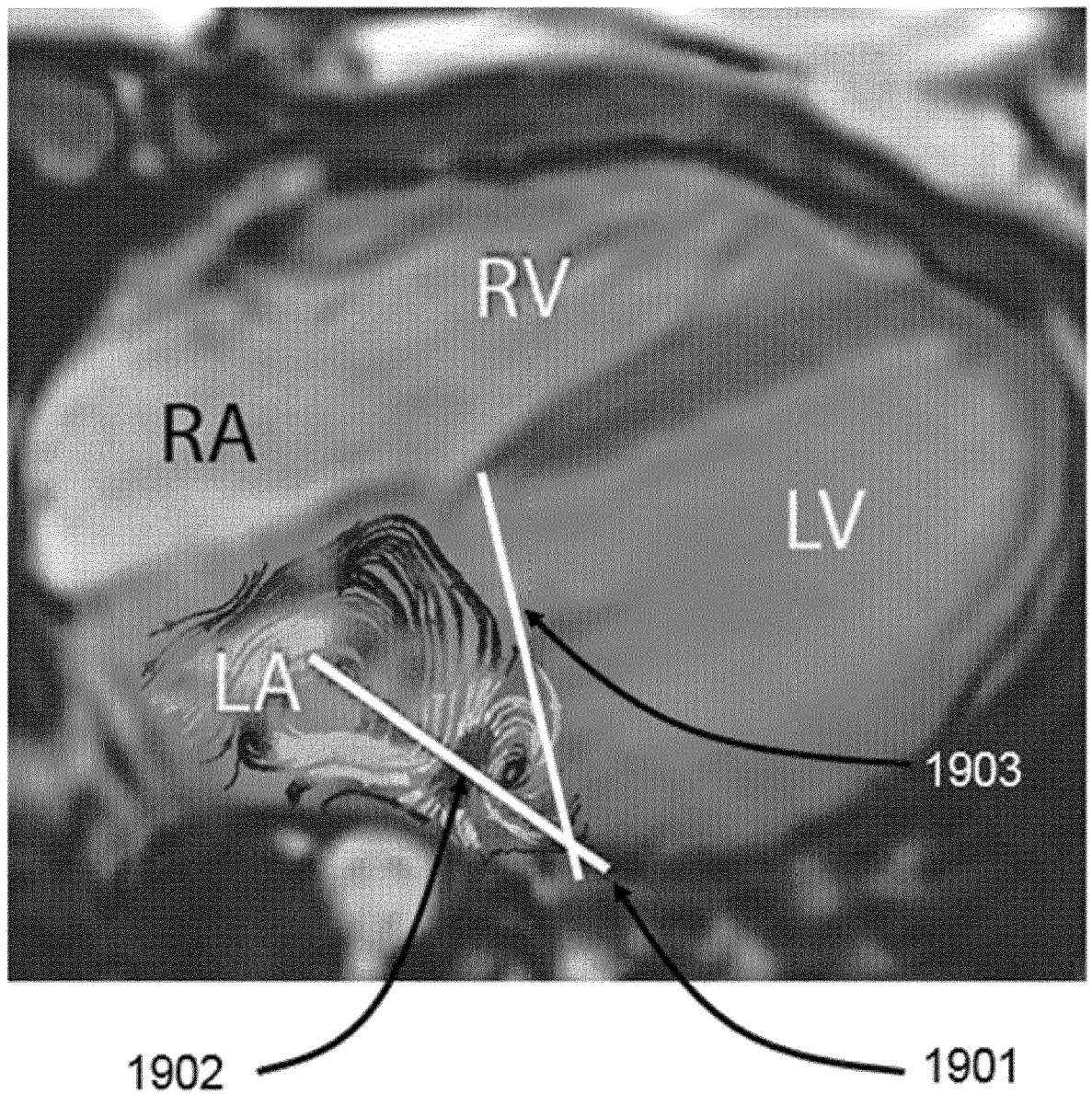
FIG. 19 shows optimal valve plane for a regurgitant jet of blood.

This step improves the accuracy of the blood flow estimation. A bias in the orientation of the analysis plane would lead to an underestimation of flow properties together with a misinterpretation of characteristic flow patterns. If the patient for instance suffers from severe regurgitation, intravoxel phase dispersion artifacts can be present in the blood flow near the heart valve and peak flow will be at a different position than at the valve level. To be able to perform an accurate analysis in such case, the plane should be optimized by repositioning the valve plane and place at the jet (as shown in FIG. 19) as described by Calkoen et al, "*Characterization and quantification of dynamic left atrioventricular valve regurgitation after atrioventricular septal defect correction with 4D Flow MRI and retrospective valve tracking*", Journal of Cardiovascular Magnetic Resonance 2014; 16(Suppl 1): P138. FIG. 19 shows a regurgitant jet of blood during systole as streamlines. These streamlines are superimposed on a 4CH long axis view. The peak jet flow is identified by 1902 and the optimal plane is identified by 1901, which is at a different location as the mitral valve plane (1903). This method is also referred to as flow tracking.

As described in step 105 of FIG. 1, quantitative analysis can be performed to assess valve dynamics on the tracked valve position. For instance, the valve motion can be quantified by computing the displacement perpendicular to the tracked valve plane which can be visualized as a displacement graph as shown by 1705 in FIG. 17. The calculated valve motion also allows for automatic correction of through plane motion during the reformatting step 111. Since step 110 optimizes the plane position/orientation, this quantification has to be performed on the new plane position.

Step 111: Reformatting

Figure 20:
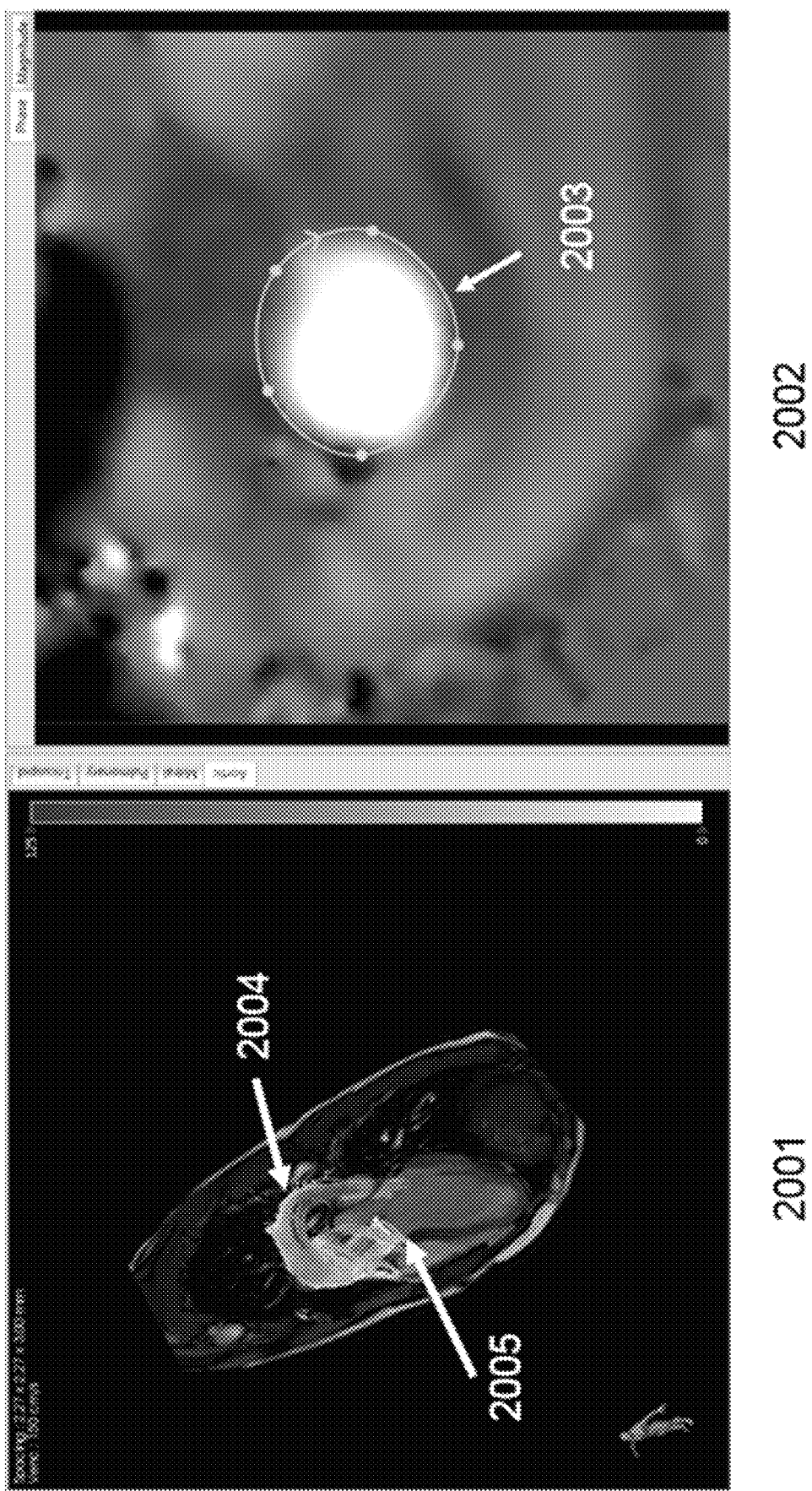
FIG. 20 shows a representation of the reformatted three-directional velocity information from 4D MR Flow data.

Based on the define valve plane (step 109 of FIG. 1) and optionally optimized by the method as described in step 110 of FIG. 1, the three-directional velocity information can optionally be reformatted into only one directional (through-plane) velocity data (step 111 of FIG. 1), since for the quantification of flow the through plane blood flow is required. This can be done in the same manner as described in Westenberg et al., "*Mitral valve and tricuspid valve blood flow: accurate quantification with 3D velocity-encoded MR imaging with retrospective valve tracking*", Radiology 2008; 249: 792-800. An example of a representation of the reformatted three-directional velocity information from 4D MR Flow data is shown in FIG. 20. FIG. 20 shows the reformatted image (2002) at the position of the aortic valve (2005). Within 2001, the streamlines emitted at the valve plane (2005) are superimposed on a LVOT1 long axis cine view. The aorta is segmented (2003) in the reformatted image (2002).

Optionally, during the reformatting the through plane velocity derived from the valve motion as explained in step 105 of FIG. 1 (with reference to FIG. 17) or recalculated after during step 110, can be corrected.

Once the velocity information has been reformatted on a 2D dynamic analysis plane for every cardiac phase, two-dimensional quantitative flow analysis is performed (step 112 of FIG. 1).

If no reformatting step is performed, 3D quantitative flow analysis is performed (step 112 of FIG. 1).

Step 112: Quantitative Flow Analysis

Before being able to perform quantitative flow analysis, the borders of the valve annulus have to be defined (FIG. 20, 2003). This can be done manually or automatically by fitting a spline through the valve positions obtained earlier as described by Lee, "*A simplified B-spline computation routine*", Computing 1982, Volume 29, Issue 4, pp 365-371. Alternative, the borders of the valve can be detected by thresholding. The thresholding method works by setting a certain value as a threshold, and any image element having a signal intensity above this threshold is marked as the object of interest, which is for instance the valve annulus (blood flow). The threshold can for instance be set as taught by N. Otsu in "*A Threshold Selection Method from Gray-Level Histograms*", IEEE Transactions on Systems, Man, and Cybernetics, vol. SMC-9, no. 1, pp. 62-66, 1979. In this method, a threshold value is calculated based on the image histogram, a table containing the occurrence frequency of each value. A threshold value is chosen to be a value that divides the histogram into two classes, which are maximally separated, and with each of the class to be as tight as possible. Alternative the threshold is based on a user click inside the blood pool. The final step is to group these image elements having values higher than the threshold and mark them as the desired feature, for instance the blood flow.

Subsequently, the velocity information obtained from the reformatted velocity data within the defined annulus area is used to quantify standard clinical parameters such as mean velocities, net flow (forward flow), retrograde flow (backward flow), pump blood volume (forward flow minus backward flow), regurgitation fraction, cardiac output, shunt, etc.

Retrograde flow can also be derived by an indirect method, this approach might be useful incase severe regurgitation is present. In addition, this approach might provide insights of the quality and/or reliability of the complete quantification process. The basic idea behind this approach is that the blood pumped into a ventricle, should be equal to the blood pumped out of the ventricle, assuming no shunts are present. For instance, for the left ventricle, during systole the amount of blood pumped out of the left ventricle should be the same as the blood pumped into the left ventricle during diastole. Taken into consideration possible leaking of the aorta and/or mitral valve (regurgitation), the forward flow of the aorta valve minus the backward flow of the mitral valve equals the forward flow of the mitral valve minus the backwards flow of the aortic valve. This means that for instance the backward mitral valve flow can be calculated based on the forward mitral valve flow and forward-, backward-aortic valve flow. The same approach can be performed for the right ventricle.

Another parameter to assess the quality and/or reliability of the complete quantification process is by comparing the net flow of all four valves. Assuming no shunts are present, the net flow of all the four valves should be equal. By computing, for instance, the standard deviation of the net flow from the four valves, the quality and/or reliability of the complete quantification process can be assessed.

Besides the above described quantitative analysis parameters, which are extracted from the reformatted velocity data (step 111), more advanced 3D quantification and/or 3D visualization can be performed. For those advanced parameters, the pressure difference, as an example of such advance 3D quantification parameter. Pressure difference is an important parameter for the location and classification of vessel lesion(s) (obstruction of a vessel due to for instance atherosclerosis). Due to the decreased orifice at a lesion, the velocity inside the lesion will be higher than inside the healthy regions of the vessel in front of and/or behind the lesion. This velocity increase causes a pressure drop in the lesion. This phenomenon is described by the Bernoulli principle. This principle states that the energy balance of a particle of fluid traveling along a tubular structure (e.g. vessel) is constant, even when passing through an orifice. Especially when the 3D optimize velocity information has not been computed, as described by step 1102, the pressure difference in vessel(s) can be computed by means of the modified Bernoulli equation as described by Bock et al, "*In Vivo Noninvasive 4D Pressure Difference Mapping in the*

Human Aorta: Phantom Comparison and Application in Healthy Volunteers and Patients", Magnetic Resonance in Medicine, vol. 66, pp. 1079-1088, 2011. This can be done on streamlines initiated from the valve plane (step 109 and/or 110), or at any plane derived from this valve plane. For instance, a certain distance more distal or more proximal to the blood flow within the valve plane. Distance can either be an Euclidean distance or a curved length distance defined by the blood flow encountered in the valve plane. To provide an example of the latter, assume the valve plane represents the aortic valve, a curved length proximal distance will follow the ascending aorta, aortic arch and descending aorta. This information is obtained from streamline analysis emitted (originated) from the valve plane.

The analysis data can also be used for quantification and/or 3D visualization purposes of the cardiovascular blood flow parameters, for instance streamlines, pathlines, particle tracing, continuous pathlines, vector fields, pressure difference, pressure gradient, wall shear stress, oscillatory shear index, energy loss, kinetic energy, turbulent kinetic energy, vorticity, and the like. The analysis can be initiated from the valve plane(s) step 109 and/or 110), or by the method as described above. It may be advantageous to use the information as obtained during step 1101 and/or 1102 to optimize the quantification of some of the above parameters. This information can for instance be used to define some geometric constraints (e.g. left ventricle, left atrium, aorta) as required during the quantification and/or visualization of particle tracing as compared to the manual approach as described by Eriksson et al, "Semi-automatic quantification of 4D left ventricular blood flow", Journal of Cardiovascular Magnetic Resonance, 2010 Feb. 12; 12:9.

Other Applications:

The embodiments described above are associated with assessing information about blood flow through the heart valve(s) based on a 4D MR Flow dataset. Alternatively, the embodiments, with special focus on the extract feature method as described in step 1102, may also be adapted to blood flow based on a 4D MR flow dataset in other areas of the body, such as, but not limited to coronary arteries, coronary veins, pulmonary arteries, pulmonary veins, aortic artery, vena cava arties.

Assessment of Blood Flow in Coronary Arteries

Figure 21:
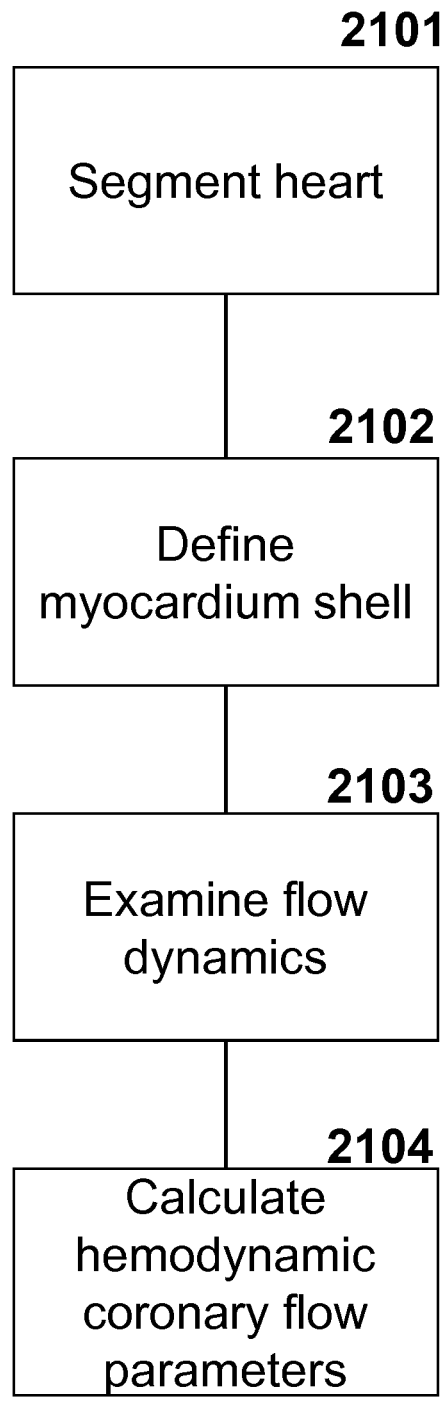
FIG. 21 shows a flowchart of a method for providing aspect of the method for assessment of blood flow in coronary arteries.

FIG. 21 shows a schematic diagram showing aspect of the method for assessment of blood flow in coronary arteries.

Step 2101 Segment Heart.

The segmented heart as described before within step 1102 of FIG. 11, can also be used for different purposes for instance coronary analysis. After the registration of the generic 3D anatomical surface model and its annotated features on the 4D MR Flow dataset (as described in step 1102) the location of the left ventricular and/or right ventricular myocardium is known (FIG. 15*b*, 1502 shows the left ventricle myocardium as well as in FIG. 22, 2204). The coronary arteries, as well as the coronary veins, are located at the epicardial surface (outer region of the myocardium), see FIG. 22. Within FIG. 22, the main coronary arteries are shown in relation to the heart. There are two main coronary arteries, the left coronary artery and the right coronary artery. The left coronary artery arises from the aorta above the left cusp of the aortic valve and feeds blood to the left side of the heart. It branches into two arteries; left anterior descending coronary artery (2201) and the left circumflex coronary artery (2202) and sometimes a third branch is formed at the fork, known as a ramus or intermediate artery. The right coronary artery (2203), originates from above the right cusp of the aortic valve. It travels down the right coronary sulcus, towards the crux of the heart.

Figure 23B:
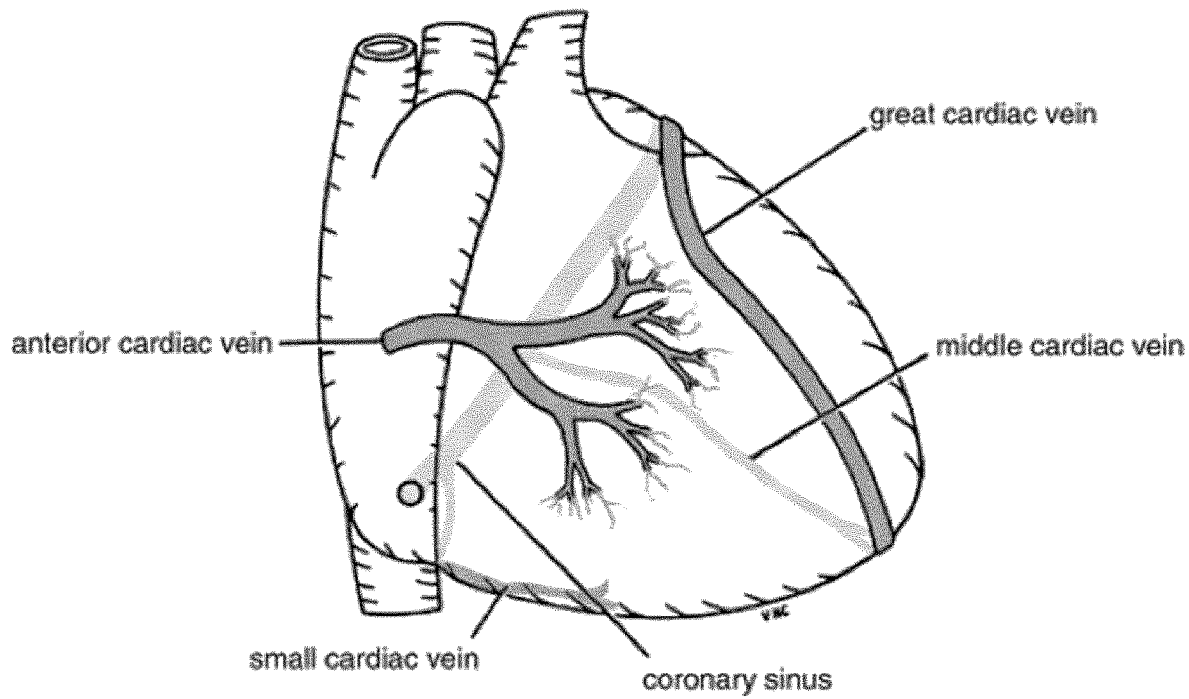
FIG. 23b shows the main coronary veins in relation to the heart.

At the epicardial surface, not only the coronary arteries are located (FIG. 23*a*), but also the coronary veins (FIG. 23*b*). The coronary arteries are the arteries of the coronary circulation that transport blood into the myocardium. The coronary veins collect and return blood from the myocardium to the right atrium through the coronary sinus.

Step 2102 Define Myocardium Shell

Figure 24:
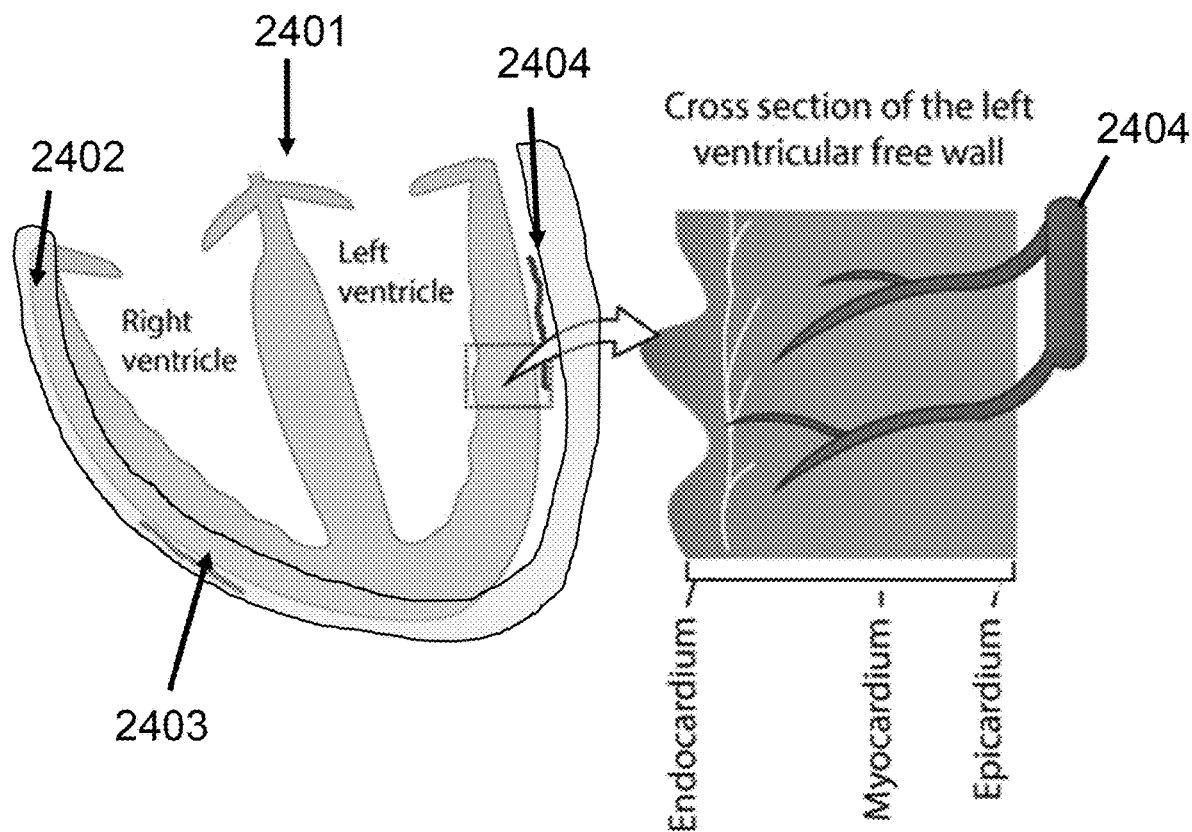
FIG. 24 shows an example of a shell surrounding the myocardium that contains the coronary arteries and coronary veins.

By indicating a shell around the myocardium starting from the epicardial side, the region of interest where the coronary vessels are located, is defined as can be seen in FIG. 24. FIG. 24 shows a schematic view of the heart in a 4CH orientation (2401). A short part of the coronary artery (2404) and of the coronary vein (2403) is identified. The shell around the myocardium is identified by 2402 and may have a predefined thickness. Alternatively, the thickness of the shell can be derived from the size of the heart chambers resulting from the segmentation process as explained before in step 1102.

Step 2103 Examine Flow Dynamics

Figure 25:
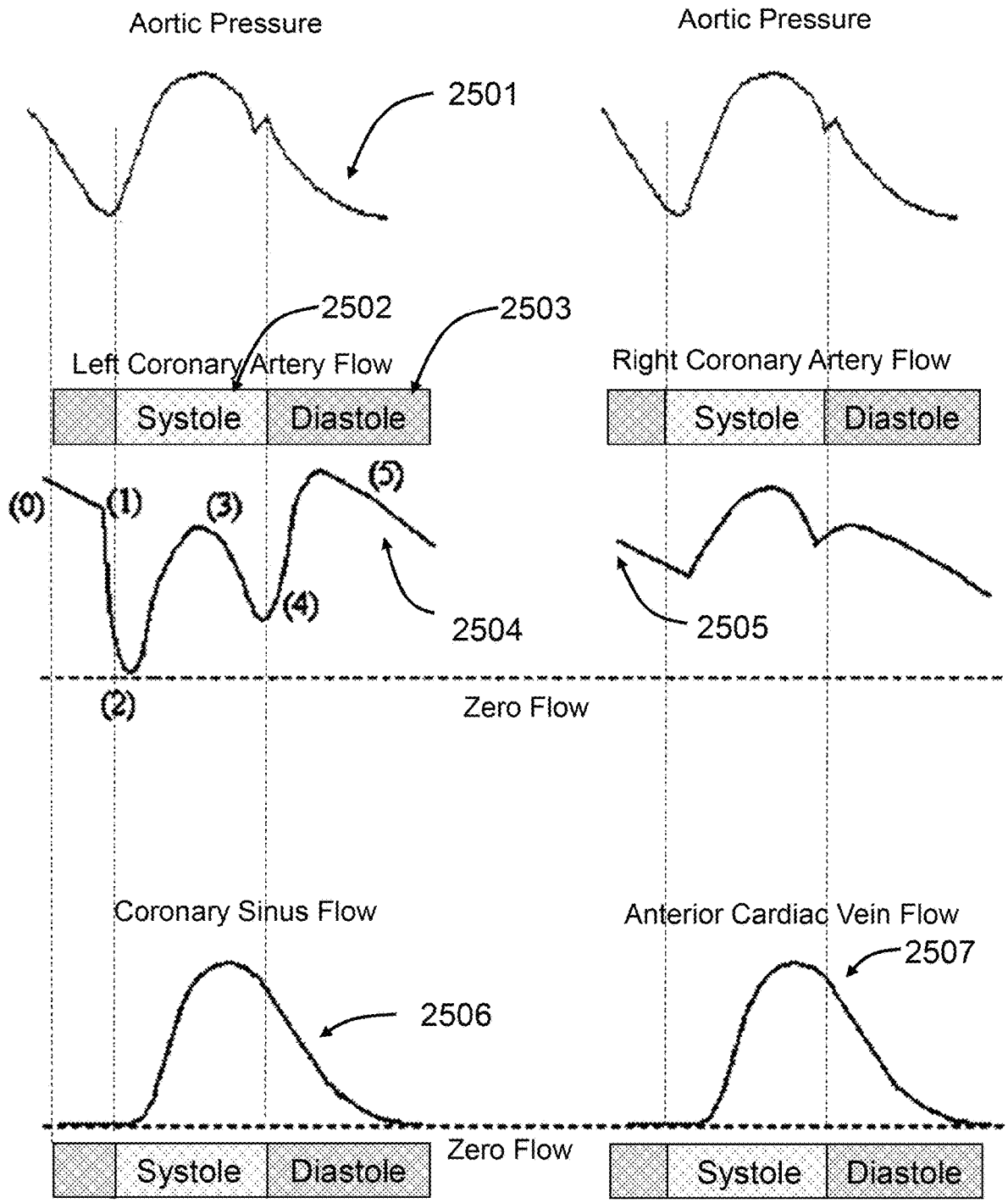
FIG. 25 shows the physiologic blood flow behavior of coronary arteries and veins.

By incorporating the physiologic flow behavior of the coronary arteries and the coronary veins, in combination with utilizing the resulting different in flow behavior, accelerations and flow dynamics within the coronary artery and coronary veins, such as performed previously within step 1101, a distinguish can be made between coronary arteries and coronary veins. To explain this method, reference is made to FIG. 25. During each phase of the cardiac cycle the extravascular pressure changes, as does the aortic pressure (2501). Since the coronary flow is determined by the ratio of the driving aortic pressure to the coronary resistance, the phasic variations in these two parameters result in a phasic change in coronary flow (2504 left coronary flow, 2505 right coronary flow). During diastole (2503), when the ventricular myocardium is relaxed, coronary flow depends primarily upon the aortic pressure (2504, label (0)). At the beginning of isovolumetric contraction phase (2504, label (1)), the extravascular pressure increases very sharply, resulting in a marked rise in coronary resistance, especially on the left side. Therefore, there is a marked decrease of the left coronary flow, such that the flow is stopped or even reversed. Following the opening of the aortic valve (2504, label (2)) the ejection of blood from the left ventricle reduces the extravascular pressure and coronary resistance. Since the aortic pressure is rising at the same time, these changes cause a rise in left coronary flow. During the period of reduced ejection (2504, label (3)), the coronary flow decreases together with aortic pressure. With the onset of isovolumetric ventricular relaxation (2504, label (4)), the extravascular pressure decreases, and the resulting reduction in coronary resistance causes a rise in left coronary flow. Thereafter (2504, label (5)), the coronary flow changes in the same direction as the arterial pressure during diastole. Because the contraction of the right ventricle is considerably weaker than that of the left ventricle, right coronary vessels are subject to much less extravascular compression during systole. The phasic tracing of right coronary blood flow follows more closely the contour of the aortic pressure tracing and resembles the flow pattern in other regions of the body.

The variations in extravascular pressure in the coronary circulation also affect the capacity of the veins and the volume of blood in the venous side of the coronary circulation. During the contraction phase as the ventricular pressure increases, the size of the veins is reduced and blood is squeezed out of the veins in the coronary circulation. As relaxation begins and ventricular pressure drops, there follows an expansion of the coronary veins and a reduction in venous outflow (2506, 2507). In addition, the flow in the coronary venous circulation is roughly the same at each location (2506, 2507).

To distinguish coronary artery flow from coronary vein flow, within the myocardium shell (2402), the above described physiologic flow behavior of coronary arteries and veins is used. By following the same approach as explained in step 1101 and with reference to FIG. 13, based on flow information from the 4D MR Flow dataset the coronary arteries are identified. Since we only look at the flow within the myocardium shell, for instance by streamline analysis, only streamlines will be visible during the cardiac cycle as a result of flow in the coronary arteries and coronary veins. Knowing the orientation of the heart (by the segmentation step as described by step 2101), and the expected location of the coronary arteries and coronary veins (FIG. 22, FIG. 23), we define a probability of each streamlines based on the direction of flow within the streamline; coronary artery flow from base of heart towards apex of heart, coronary venous flow in opposite direction. Next, we can define a probability of each streamlines based on the expected flow dynamics within the cardiac cycle of the left coronary artery (2504), right coronary artery (2505) and coronary veins (2506, 2507). For instance, during systole (2502), left coronary artery flow significantly decrease as coronary venous flow significant increases. By weighting the calculated probabilities from above, only the streamlines from the coronary arteries can be identified. The method as described in step 2103 is based by using streamlines which are derived from the 4D MR Flow dataset as an example and is not restricted to streamlines approach. In fact, the method of step 2103 utilizes the different in flow behavior, accelerations and flow dynamics within the coronary arteries and coronary veins during the cardiac cycle and different 4D flow quantification techniques can be used. Such as instantaneous streamlines, pathlines, particle tracing, kinetic energy, turbulent kinetic energy, vorticity, etc.

Step 2104 Calculate Hemodynamic Coronary Flow Parameters.

Once the streamlines resulting from flow within the coronary arteries are identified, and such localize the coronary arteries, hemodynamic blood flow parameters can be quantified. Optionally, the coronary arties can be segmented. For instance, the coronary arteries can be segmented by means of a 3D deformable segmentation method (Xu et al, J. 2000. *Medical Image Segmentation Using Deformable Models. SPIE Press*, Chapter 3, 129-174) which is guided by the streamlines resulting from flow within the coronary arteries. Hemodynamic blood flow parameters quantified can be for instance, wall shear stress, pressure gradient, pressure drop, instantaneous wave-free ratio, fractional flow reserve, coronary flow reserve and the like. The analysis data can also be used for 3D visualization purposes of the coronary artery blood flow (for instance streamlines, pathlines, particle tracing, continuous pathlines, wall shear stress, vector fields, pressure difference, and the like). To allow calculation of fractional flow reserve and/or coronary flow reserve an addition step is required. Both coronary flow reserve and fractional flow reserve relates to maximum blood flow (during exercise) through a coronary artery. The energy required to support the pumping activity of the heart varies highly between rest and exercise. Thus, in addition to the increase in cardiac output, the coronary circulation has the capacity to increase the coronary blood flow to the heart during exercise by reducing the resistance of the coronary circulation. This excess capacity is called the coronary flow reserve. On the other hand, the fractional flow reserve is defined as the ratio of maximum blood flow distal to a stenotic lesion to normal maximum flow in the same vessel. Since, the 4D MR Flow dataset is normally acquired during rest, we need to estimate the flow during exercise of the subject under examination. This can be done by a fixed value. This value represents the increase in blood flow in exercise as compared to rest as described by Zijlstra et al., "*The ideal coronary vasodilator for investigating coronary flow reserve? A study of timing, magnitude, reproducibility, and safety of the coronary hyperemic response after intracoronary papaverine*", Catheterization and Cardiovascular Diagnosis", 1986, 298-303, in which they established a relation between rest and hyperemic coronary flow. Additional the fixed value can be made subject specific by incorporating information as obtained during step 2101 and/or 2102. For instance, the volume of the myocardium mass can be used to weight the fixed value.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS or VNA commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for performing flow analysis in a three-dimensional (3D) target volume of a moving organ having a long axis, the method comprising:
   a) acquiring a four-dimensional (4D) MR Flow volumetric image data set of the target volume, wherein the 4D MR Flow volumetric image data set comprises anatomical information of the target volume and three-directional velocity information of fluid flow in the target volume over time;
   b) tracking position over time of at least one feature of interest within the 4D MR Flow volumetric image data set or in a derived two-dimensional (2D) image data set or three-dimensional surface model derived from the 4D MR Flow volumetric image data set;
   c) determining spatial position and orientation over time of at least one plane containing the at least one feature of interest in the 4D MR Flow volumetric image data set from the tracking of b); and
   d) performing quantitative flow analysis using the velocity information of the 4D MR Flow volumetric image data set that corresponds to the at least one plane as determined in c).

2. The method according to claim 1, where the derived 2D image data set is related to the long axis of the moving organ and is created by multi planar reconstruction.

3. The method according to claim 1, wherein position of the at least one feature of interest is determined by receiving input from a user or by performing automatic feature detection on the 4D MR Flow volumetric image data set.

4. The method according to claim 3, wherein the automatic feature detection comprises analyzing flow dynamics using the 4D MR Flow volumetric image data set to determine the position of the at least one feature of interest.

5. The method according to claim 4, wherein the analyzing flow dynamics is based on flow quantification techniques selected from a group consisting of: instantaneous streamlines, pathlines, particle tracing, kinetic energy, vorticity or turbulent kinetic energy.

6. The method according to claim 3, wherein the automatic feature detection comprises machine learning to determine the position of the at least one feature of interest.

7. The method according to claim 3, further comprising translating the at least one feature of interest to the derived 2D image data set.

8. The method according to claim 7, further comprising using user input to adjust position of the at least one feature of interest in the derived 2D image data set as determined from the automatic feature detection.

9. The method according to claim 1, wherein the derived 2D image data set is based upon at least one landmark specified by a user or automatic generation steps performed on the 4D MR Flow volumetric image data set.

10. The method according to claim 9, wherein the at least one landmark is specified by user input with respect to a static 3D volume.

11. The method according to claim 9, wherein the derived 2D image data set is obtained by generating images parallel to the normal of a plane perpendicular to fluid flow.

12. The method according to claim 9, wherein the automatic generation steps comprise registering the 4D MR Flow volumetric data set with a three-dimensional (3D) anatomical surface model with annotated features to use as landmarks.

13. The method according to claim 1, wherein the tracking of position over time of the at least one feature of interest is performed on the derived 2D image data set by matching at least one two-dimensional template to the derived 2D image set.

14. The method according to claim 13, wherein the template matching involves cross correlation.

15. The method according to claim 1, wherein the tracking of position over time of the at least one feature of interest involves image registration.

16. The method according to claim 1, wherein the quantitative flow analysis is performed on one-direction velocity information obtained by reformatting the three-directional velocity information on the at least one plane as determined in c).

17. The method according to claim 1, wherein the orientation of the at least one plane containing the at least one feature of interest in the 4D MR Flow volumetric image data set is adjusted to render it perpendicular to the fluid flow through the at least one feature of interest.

18. The method according to claim 1, wherein the three-directional velocity information is reformatted into one-directional velocity information for the at least one plane.

19. The method according to claim 1, wherein feedback is provided on the tracking of position over time of the at least one feature of interest.

20. The method according to claim 1, wherein the tracking of position over time of the at least one feature of interest is performed within the 4D MR Flow volumetric image data set by matching multiple volumetric templates to the 4D MR Flow volumetric image data set.

21. The method according to claim 20, wherein the volumetric templates have a variable size depending on image acquisition resolution.

22. The method according to claim 1, wherein the quantitative flow analysis is based on flow parameters selected from a group consisting of: mean velocities, forward flow), backward flow, pump blood volume, regurgitation fraction, cardiac output, shunt, streamlines, pathlines, particle tracing, continuous pathlines, vector fields, pressure difference, pressure gradient, wall shear stress, oscillatory shear index, energy loss, kinetic energy, turbulent kinetic energy, vorticity.

23. The method according to claim 1, wherein the moving organ is a heart of a patient, the target volume is a region of the heart comprising a heart valve, and the at least one feature of interest comprises the heart valve.

24. The method according to claim 23, wherein the position of the at least one feature of interest is determined by combining information at end-diastole and end-systole.

25. A non-transitory computer readable media comprising software code portions directly loadable into memory of a digital computer for performing the method according to claim 1 when the software code portions are executed by the digital computer.

26. An MR apparatus for acquiring 4D MR Flow volumetric image data sets, the MR apparatus comprising a data acquisition system for obtaining time resolved three-dimensional phase contrast MRI image volumes of a heart of a patient, and the MR apparatus further comprising a processor programmed for performing the method according to claim 1 to make a quantitative blood flow analysis.

27. The MR apparatus according to claim 26, wherein the data acquisition system is configured to acquire 4D flow images of a volume containing a heart valve, the processor being programmed to locate a plane containing the heart valve in the 4D flow images and make a bi-dimensional flow analysis based on velocity information as projected on the plane containing the heart valve.

28. The MR apparatus according to claim 27, wherein the orientation of the valve plane is determined by performing valve tracking after the 4D flow images have been acquired.

29. The method according to claim 1, wherein a)-d) are performed by a processor.

30. The method according to claim 1, wherein the 4D MR Flow volumetric image data set is obtained by phase contrast MR imaging of the target volume.

31. The method according to claim 1, wherein the quantitative flow analysis of d) uses the velocity information of the 4D MR Flow volumetric image data set that corresponds to spatial position and orientation of the at least one plane as determined in c).

32. The method according to claim 1, wherein the derived 2D image data set is related to the long axis of the moving organ and comprises two dimensional images that are constructed from the 4D MR Flow volumetric image data set or from volumetric image data of a static three-dimensional volume constructed from the 4D MR Flow volumetric image data set.

33. The method according to claim 1, wherein the derived 2D image data set is related to the long axis of the moving organ and comprises two dimensional images that are constructed from the 4D MR Flow volumetric image data set based upon user input specifying a landmark associated with the at least one feature of interest.

34. The method according to claim 33, wherein the landmark comprises a reference line or point.

35. The method according to claim 1, wherein the derived 2D image data set is related to the long axis of the moving organ and comprises two dimensional images based upon a three-dimensional anatomical surface model constructed from the 4D MR Flow volumetric image data set.

36. The method according to claim 1, wherein the derived 2D image data set is based upon at least one landmark determined automatically by analyzing flow dynamics.

37. The method according to claim 36, wherein the analyzing flow dynamics is based on flow quantification techniques selected from a group consisting of: instantaneous streamlines, pathlines, particle tracing, kinetic energy, vorticity or turbulent kinetic energy.

38. The method according to claim 1, wherein the tracking of the position of the at least one feature of interest is performed on the volumetric image data set by matching at least one three-dimensional template to the 4D MR Flow volumetric image data set.

39. The method according to claim 38, wherein the template matching involves cross correlation.

* * * * *